(12) United States Patent
Elzein et al.

(10) Patent No.: US 6,946,449 B2
(45) Date of Patent: Sep. 20, 2005

(54) PARTIAL AND FULL AGONISTS OF A1 ADENOSINE RECEPTORS

(75) Inventors: Elfatih Elzein, Fremont, CA (US); Prabha Ibrahim, Mountain View, CA (US); Venkata Palle, Sunnyvale, CA (US); Vaibhav Varkhedkar, Mountain View, CA (US); Jeff Zablocki, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 375 days.

(21) Appl. No.: 10/194,335

(22) Filed: Jul. 11, 2002

(65) Prior Publication Data

US 2003/0050275 A1 Mar. 13, 2003

Related U.S. Application Data

(60) Provisional application No. 60/305,329, filed on Jul. 13, 2001.

(51) Int. Cl.$^7$ .......................... A61K 31/70; C07H 19/16; C07H 19/167
(52) U.S. Cl. ...................... 514/46; 514/263.1; 514/266; 536/27.3; 536/27.63; 544/264
(58) Field of Search .................... 514/261, 46, 266, 514/263.1; 544/262, 264; 536/27.3, 27.63

(56) References Cited

U.S. PATENT DOCUMENTS 6,258,793 B1    7/2001    Palle et al.

FOREIGN PATENT DOCUMENTS

| EP | 0181129 A2 | 5/1986 |
|---|---|---|
| RO | 116 401 B | 1/2001 |
| WO | WO 99/24449 A2 | 5/1999 |
| WO | WO 99/24450 A2 | 5/1999 |
| WO | WO 99/24451 A2 | 5/1999 |
| WO | WO 99/67262 A1 | 12/1999 |
| WO | WO 99/67262 | * 12/1999 |
| WO | WO 01/40243 | 6/2001 |

OTHER PUBLICATIONS

Tilburg et al, J. Med. Chem., vol. 42, pp. 1393–1400.*
Brackett L E et al: "Functional Characterization of the A2B Adenosine Receptor in NIH 3T3 Fibroblasts", Biochemical Pharmacology, Pergamon, Oxford, GB, vol. 47, No. 5, 1994, pp. 801–814 XP000942545, ISSN: 0006–2952 abstract.
Marumoto R et al: "Synthesis and Enzymatic Activity of Adenosine 3', 5'–Cyclic Phosphate Analogs", Chemical and Pharmaceutical Bulletin, Pharmaceutical Society of Japan. Tokyo, JP., vol. 27, No. 4, 1979, pp. 990–1003, ISSN: 0009–2363, "chart 3", p. 992, table 3.
Munro R et al, "Differential expression of adenosine A2A and A2B receptor subtypes of myeloid U937 and THP–1 cells: Adenosine A2B receptor activation selectively stimulates cAMP formation and inhibition of TNFalpha release in THP–1 cells," Drug Development Research, vol. 44, No. 1, May 1998, pp. 41–47 ISSN: 0272–4391.
Van Der Wenden, E. et al: "5'–Substituted adenosine analogs as new high–affinity partial agonists for the adenosine A1 receptor", J. Med Chem, 1998, 41, pp. 102–108.
Tilburg, E. et al: "N6.5'–Disubstituted adenosine derivatives as partial agonists for the human adenosine A3 receptor", J. Med. Chem, 1999, 42, pp. 1393–1400.
R.M. Smejkal et al. (1989) "Muscarinic receptor subtype specificity of 5'(isobutylthio)–adenosine (SIBA) and its analogues," Gen. Pharmac., 20(3):385–392, XP008022164.

* cited by examiner

*Primary Examiner*—James O. Wilson
*Assistant Examiner*—Howard V. Owens, Jr.
(74) *Attorney, Agent, or Firm*—Brian Lewis; Pauline Ann Clarke; J. Elin Hartrum

(57) ABSTRACT

Disclosed are novel compounds that are partial and full $A_1$ adenosine receptor agonists, useful for treating various disease states, in particular tachycardia and atrial flutter, angina, and myocardial infarction.

30 Claims, No Drawings

PARTIAL AND FULL AGONISTS OF A1 ADENOSINE RECEPTORS

FIELD OF THE INVENTION

The present invention relates to novel compounds that are partial or full $A_1$ adenosine receptor agonists, and to their use in treating mammals for various disease states, including modifying cardiac activity, in particular treatment of arrhythmia. The compounds are also useful for treating CNS disorders, diabetic disorders, obesity, and modifying adipocyte function. The invention also relates to methods for their preparation, and to pharmaceutical compositions containing such compounds.

BACKGROUND

Adenosine is a naturally occurring nucleoside, which exerts its biological effects by interacting with a family of adenosine receptors known as $A_1$, $A_{2a}$, $A_{2b}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148–153), and $A_3$ adenosine receptors modulate cell proliferation processes.

The $A_1$ adenosine receptor mediates two distinct physiological responses. Inhibition of the cardiostimulatory effects of catecholamine is mediated via the inhibition of adenylate cyclase, whereas the direct effects to slow the heart rate (HR) and to prolong impulse propagation through the AV node are due in great part to activation of $I_{KAdo}$. (B. Lerman and L. Belardinelli Circulation, Vol. 83 (1991), P 1499–1509 and J. C. Shryock and L. Belardinelli The Am. J. Cardiology, Vol. 79 (1997) P 2–10). Stimulation of the $A_1$ adenosine receptor shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter.

Accordingly, $A_1$ adenosine agonists are useful in the treatment of acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter. Exposure to $A_1$ agonists causes a reduction in the heart rate and a regularization of the abnormal rhythm, thereby improving cardiovascular function.

$A_1$ agonists, through their ability to inhibit the effects of catecholamines, decrease cellular cAMP, and thus have beneficial effects in the failing heart where increased sympathetic tone increases cellular cAMP levels. The latter condition has been shown to be associated with increased likelihood of ventricular arrhythmias and sudden death. See, for example, B. Lerman and L. Belardinelli Circulation, Vol. 83 (1991), P 1499–1509 and J. C. Shryock and L. Belardinelli, Am. J. Cardiology, Vol. 79 (1997) P 2–10.

$A_1$ agonists, as a result of their inhibitory action on cyclic AMP generation, have antilipolytic effects in adipocytes that leads to a decreased release of nonesterified fatty acids (NEFA) (E. A. van Schaick et al J. Pharmacokinetics and Biophamaceutics, Vol. 25 (1997) p 673–694 and P. Strong Clinical Science Vol. 84 (1993) p. 663–669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis (D. Thiebaud et al Metab. Clin. Exp. Vol. 31 (1982) p 1128–1136 and G. Boden et al J. Clin. Invest. Vol. 93 (1994) p 2438–2446). The hypothesis of a glucose fatty acid cycle was proposed by P. J. Randle as early as 1963 (P. J. Randle et al Lancet (1963) p. 785–789). A tenet of this hypothesis would be that limiting the supply of fatty acids to the peripheral tissues should promote carbohydrate utilization (P. Strong et al Clinical Science Vol. 84 (1993) p. 663–669).

The benefit of an $A_1$ agonist in central nervous disorders has been reviewed (L. J. S. Knutsen and T. F. Murray in Purinergic Approaches in Experimental Therapeutics, Eds. K. A. Jacobson and M. F. Jarvis (1997) Wiley-Liss, N. Y., P-423–470). Briefly, based on experimental models of epilepsy, a mixed $A_{2A}$: $A_1$ agonist, metrifudil, has been shown to be a potent anticonvulsant against seizures induced by the inverse benzodiazepine agonist methyl 6,7-dimethoxy-4-ethyl-beta-carboline-3-carboxylate (DMCM, H. Klitgaard Eur. J. Pharmacol. (1993) Vol. 224 p. 221–228). In other studies using CGS 21680, an $A_{2A}$ agonist, it was concluded that the anticonvulsant activity was attributed to activation of the $A_1$ receptor (G. Zhang et al. Eur. J. Pharmacol. Vol. 255 (1994) p. 239–243). Furthermore, $A_1$ adenosine selective agonists have been shown to have anticonvulsant activity in the DMCM model (L. J. S. Knutsen In Adenosine and Adenne Nucleotides: From Molecular Biology to Integrative Physiology; eds. L. Belardinelli and A. Pelleg, Kluwer: Boston, 1995, pp 479–487). A second area where an $A_1$ adenosine agonist has a benefit is in animal models of forebrain ishemia as demonstrated by Knutsen et al (J. Med. Chem. Vol. 42 (1999) p. 3463–3477). The benefit in neuroprotection is believed to be in part due to the inhibition of the release of excitatory amino acids (ibid).

Adenosine itself has proven effective in treating disease states related to the $A_1$ adenosine receptor, for example in terminating paroxysmal supraventricular tachycardia. However, these effects are short-lived because adenosine's half-life is less than 10 sec. Additionally, as adenosine acts indiscriminately on the $A_{2A}$, $A_{2B}$, and the $A_3$ adenosine receptor subtypes, it also provides direct effects on sympathetic tone, coronary vasodilatation, systemic vasodilatation and mast cell degranulation.

Accordingly, it is an object of this invention to provide compounds that are potent full $A_1$ adenosine receptor agonists or partial $A_1$ receptor agonists with a half life greater than that of adenosine, and that are selective for the $A_1$ adenosine receptor, which will ensure that undesired side effects related to stimulation or antagonism of the other adenosine receptors are avoided.

SUMMARY OF THE INVENTION

It is an object of this invention to provide compounds that are selective, partial or full $A_1$ receptor agonists. Accordingly, in a first aspect, the invention relates to compounds of Formula I:

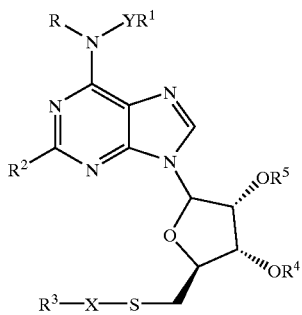

Formula I wherein:

R is hydrogen or lower alkyl;

$R^1$ is optionally substituted alkyl, optionally substituted cycloalkyl, optionally substituted aryl, or optionally substituted heteroaryl; or R and $YR^1$ when taken together with the nitrogen atom to which they are attached represents optionally substituted heterocyclyl;

$R^2$ is hydrogen, halo, trifluoromethyl, acyl, or cyano;

$R^3$ is optionally substituted cycloalkyl, optionally substituted aryl; optionally substituted heteroaryl, or optionally substituted heterocyclyl, $R^4$ and $R^5$ are independently hydrogen or acyl; and X and Y are independently a covalent bond or optionally substituted alkylene;

with the proviso that when $R^1$ is methyl and Y is a covalent bond, $R^3$ cannot be phenyl when X is methylene or ethylene.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that can be usefully treated with a partial or full selective $A_1$ receptor agonist. Such diseases include atrial fibrillation, supraventricular tachycardia and atrial flutter, congestive heart failure, antilipolytic effects in adipocytes, epilepsy, stroke, diabetes, obesity, ischemia, including stable angina, unstable angina, cardiac transplant, and myocardial infarction.

Of the compounds of Formula I, one preferred class includes those in which $R^3$ is optionally substituted aryl or optionally substituted heteroaryl, especially where R, $R^2$, $R^4$ and $R^5$ are all hydrogen.

Of these compounds, one preferred group includes compounds in which $R^3$ is optionally substituted aryl, especially those in which $R^3$ is optionally substituted phenyl, $R^1$ is optionally substituted cycloalkyl, and X is a covalent bond. A preferred subgroup includes those compounds in which $R^3$ is phenyl substituted by halo, especially fluoro, and $R^1$ is optionally substituted cyclopentyl, especially 2-hydroxycyclopentyl.

A second preferred subgroup includes compounds in which $R^1$ and $R^3$ are both optionally substituted phenyl, X is a covalent bond, and Y is optionally substituted lower alkylene, especially those compounds in which Y is ethylene, propylene or propylene substituted by phenyl.

A third preferred subgroup includes compounds in which $R^1$ is optionally substituted alkyl or optionally substituted phenyl, $R^3$ is optionally substituted phenyl, and X and Y are both covalent bonds. A preferred subgroup includes those compounds in which $R^1$ is lower alkyl or 2-fluorophenyl and $R^3$ is phenyl or 2-fluorophenyl.

Another preferred group includes compounds in which $R^3$ is optionally substituted heteroaryl, especially those in which $R^3$ is optionally substituted 1,3-thiazol-2-yl or optionally substituted 1,3-benzoxazol-2-yl. A preferred subgroup includes those compounds in which $R^1$ is optionally substituted cycloalkyl or optionally substituted phenyl, X is a covalent bond, and Y is a covalent bond or alkylene. A more preferred subgroup includes those compounds in which $R^1$ is bicycloalkyl, particularly bicyclo[2.2.1]hepty-2-yl, and Y is a covalent bond, or $R^1$ is monocyclic, especially cyclopropyl, and Y is methylene. Another preferred subgroup includes those compounds in which $R^1$ is phenyl and Y is lower alkylene.

A second preferred class includes those compounds in which $R^2$, $R^4$ and $R^5$ are all hydrogen, and R and $YR^1$ when taken together with the nitrogen to which they are attached represent a nitrogen containing heterocyclyl. A preferred group includes those compounds in which $R^3$ is optionally substituted phenyl or optionally substituted heteroaryl and X is a covalent bond, especially where R and $YR^1$ when taken together with the nitrogen to which they are attached represents pyrrolidin-1-yl.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1–5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both from 1 to 5 substituents as defined above and is also interrupted by 1–5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1–5 atoms as defined for substituted alkyl, or a lower alkyl group as defined above that has both from 1 to 5 substituents as defined above and is also interrupted by 1–5 atoms as defined above.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1–5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both from 1 to 5 substituents as defined above and is also interrupted by 1–20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxyethoxy)ethane (—CH$_2$CH$_2$O—CH$_2$CH$_2$—OCH$_2$CH$_2$—OCH$_2$CH$_2$—), and the like.

The term "aralkyl: refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is; optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or propynyl, —C≡CCH$_3$), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —$NH_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl,. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, or —$S(O)_nR$, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

The compounds of Formula I include the definition that "R and $YR^1$ when taken together with the nitrogen atom to which they are attached represents optionally substituted heterocyclyl". Such a definition includes heterocycles with only nitrogen in the ring, for example pyrrolidines and piperidines, and also includes heterocycles that have more than one heteroatom in the ring, for example piperazines, morpholines, and the like.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —$S(O)_2R$, in which R is alkyl, aryl, or heteroaryl. "Substituted sulfone" refers to a group —$S(O)_2R$, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl) amines, alkenyl amines, dialkenyl amines, trialkenyl amines, substituted alkenyl amines, di(substituted alkenyl) amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and triamines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A compound that is an agonist with high intrinsic efficacy evokes the maximal effect of which the biological system is capable. These compounds are known as "full agonists". They are able to elicit the maximum possible effect without occupying all the receptors, if the efficiency of coupling to the effector process is high. In contrast, "partial agonists" evoke a response but cannot evoke the maximal response of which the biological system is capable. They may have reasonable affinity but low intrinsic efficacy. Partial $A_1$ adenosine agonists may have an added benefit for chronic therapy because they will be less likely to induce desensitization of the $A_1$ receptor (R. B. Clark, B. J. Knoll, R. Barber TiPS, Vol. 20 (1999) p. 279–286), and less likely to cause side effects.

Nomenclature

The naming and numbering of the compounds of the invention is illustrated with a representative compound of Formula I in which R is hydrogen, $R^1$ is 2-hydroxycycloalkyl, $R^2$ is hydrogen, $R^3$ is 2-fluorophenyl, $R^4$ and $R^5$ are both hydrogen, and X and Y are both covalent bonds:

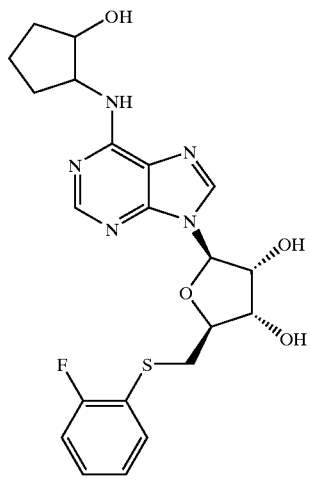

which is named:
(4S,5S,2R,3R)-5-[(2-fluorophenylthio)methyl]-2-{6-[(2-hydroxycyclopentyl)amino]-purin-9-yl}oxolane-3,4-diol.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

The compounds of Formula I may be prepared starting from 2,6-dichloropurine, as shown in Reaction Scheme I.

REACTION SCHEME I

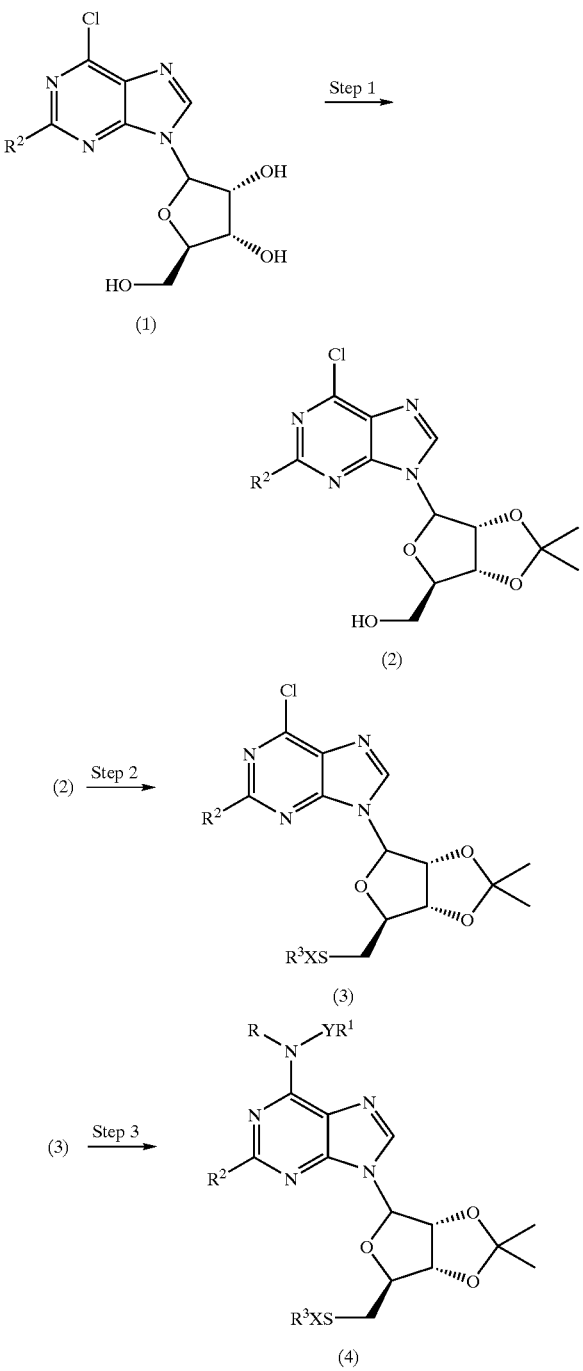

-continued

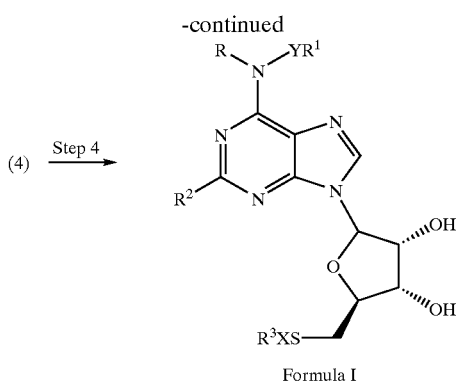

Formula I

Step 1—Preparation of Formula (2)

The starting compound of formula (1) is prepared as previously described in U.S. Pat. No. 5,789,416, the complete disclosure of which is incorporated by reference.

The compound of formula (2) is prepared conventionally from the compound of formula (1), by reaction with 2,2-dimethoxypropane in an inert solvent, preferably dimethylformamide, in the presence of a catalytic amount of an acid catalyst, preferably p-toluenesulfonic acid, at a temperature of about 40–90° C., preferably about 70° C., for about 24–72 hours, preferably about 48 hours. When the reaction is substantially complete, the product of formula (2) is isolated by conventional means, for example removal of the solvent under reduced pressure and purifying the residue by flash chromatography.

Step 2—Preparation of Formula (3)

The compound of formula (2) is then converted to a compound of formula (3). The compound of formula (2) is reacted with a thio compound of formula $R^3SH$, where $R^3$ is as defined above, in the presence of a triphenylphosphine and diethylazodicarboxylate, in an inert solvent, preferably an ether, more preferably tetrahydrofuran. The reaction is preferably conducted at reflux, for about 24–100 hours, preferably about 72 hours. When the reaction is substantially complete, the product of formula (3) is isolated by conventional means, for example removal of the solvent under reduced pressure and purifying the residue by flash chromatography.

Step 3—Preparation of Formula (4)

The 2-chloro moiety is then displaced from the compound of formula (3) by reaction with an amine of formula $RR^1YNH_2$, where Y is a covalent bond or alkylene, in the presence of a base, preferably triethylamine. The reaction is carried out in an inert protic solvent, preferably ethanol, at a temperature of about reflux, for about 14–48 hours, preferably about 24 hours. When the reaction is substantially complete, the product of formula (4) is isolated by conventional means, for example by removal of the solvent under reduced pressure, followed by chromatography of the residue on silica gel.

Step 4—Preparation of Formula I

The compound of formula (4) is then deprotected by treatment with an acid, preferably an organic acid, for example acetic acid. The reaction is carried out in a mixture of the acid and water, at about 50–100° C., preferably about 80–90° C., for about 10–48 hours, preferably about 16 hours. When the reaction is substantially complete, the product of Formula I is isolated by conventional means, for example by removal of the solvent under reduced pressure, followed by chromatography of the residue on silica gel.

It should be noted that steps 2 and 3 can be carried out in the reverse order.

Alternative Synthesis of the Compounds of Formula I

Alternatively, the compounds of Formula I may be prepared as shown in Reaction Scheme II.

REACTION SCHEME II

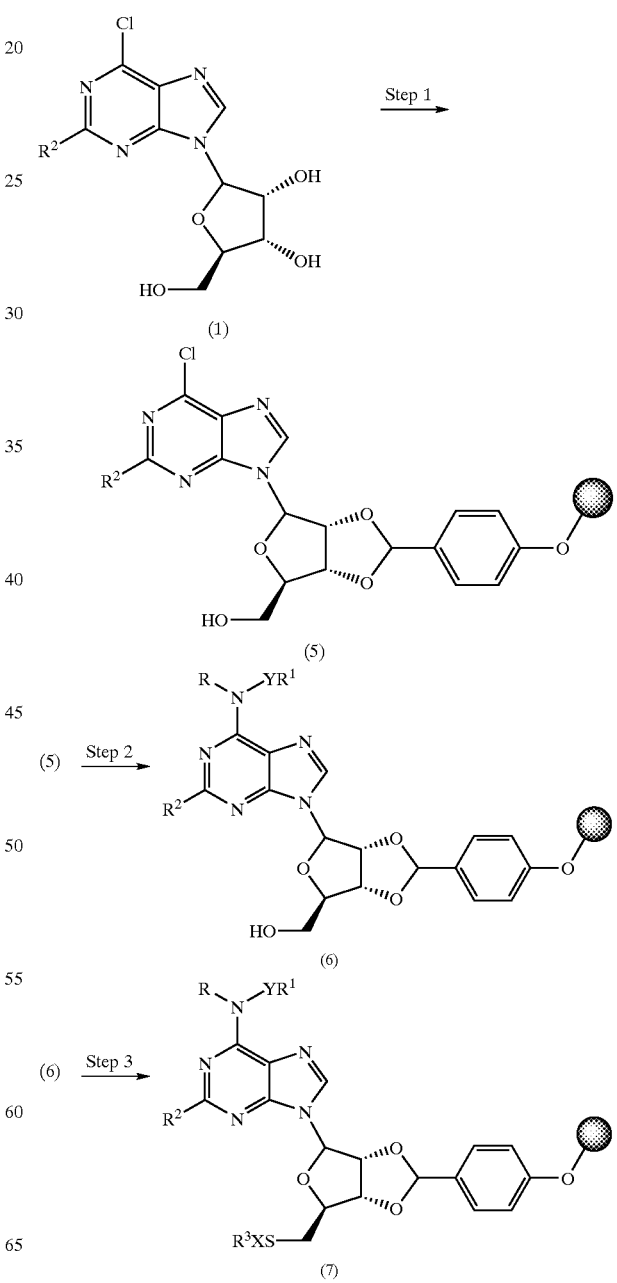

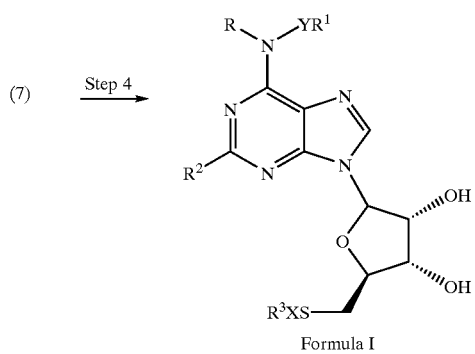

Formula I

⬤ represents a resin

Step 1—Preparation of Formula (5)

The resin/compound of formula (5) is prepared from the compound of formula (1), by reaction with dimethylacetal resin in an inert solvent, preferably dimethylacetamide, in the presence of a catalytic amount of an acid catalyst, preferably 10-camphorsulfonic acid, at about room temperature, for about 1–7 days, preferably about 4 days. When the reaction is substantially complete, the resin/product of formula (5) is isolated by conventional means, for example filtration.

Step 2—Preparation of Formula (6)

The 2-chloro moiety is then displaced from the resin/compound of formula (5) by reaction with an amine of formula $RR^1YNH_2$, where Y is a covalent bond or alkylene, in the presence of a base, preferably diisopropylethylamine. The reaction is carried out in an inert protic solvent, preferably 1,4-dioxane, at a temperature of about 80° C. for about 14–96 hours, preferably about 48 hours. When the reaction is substantially complete, the resin/product of formula (6) is isolated by conventional means.

Step 3—Preparation of Formula (7)

The product of formula (6) is then converted to a resin/compound of formula (7). The resin/compound of formula (6) is initially reacted with a compound capable of forming a leaving group, preferably methanesulfonyl chloride, in the presence of a base, preferably diisopropylethylamine, at about 0° C. The mesylated product is then reacted with a thio compound of formula $R^3XSH$, where $R^3$ and X are as defined above, in an inert solvent, preferably aqueous acetonitrile. The reaction is preferably conducted at about reflux, for about 24–100 hours, preferably about 70 hours. When the reaction is substantially complete, the product of formula (7) is isolated by conventional means, for example filtration.

Step 4—Preparation of Formula I

The resin/compound of formula (7) is then deprotected by treatment with an acid, preferably an organic acid, for example 2% trifluoroacetic acid/5% methanol/methylene chloride. The reaction is carried out at about room temperature for about 30 minutes to 10 hours, preferably about 2 hours. When the reaction is substantially complete, the product of Formula I is isolated by conventional means, for example extraction with an inert solvent, preferably methylene chloride, and removal of the solvent from the extract by evaporation under reduced pressure.

Starting Materials

Compounds of formula (1) in which $R^2$ is not hydrogen may be prepared by methods well known in the art. For example, the preparation of a compound of formula (1) in which $R^2$ is trifluoromethyl is prepared as shown in Reaction Scheme III.

REACTION SCHEME III

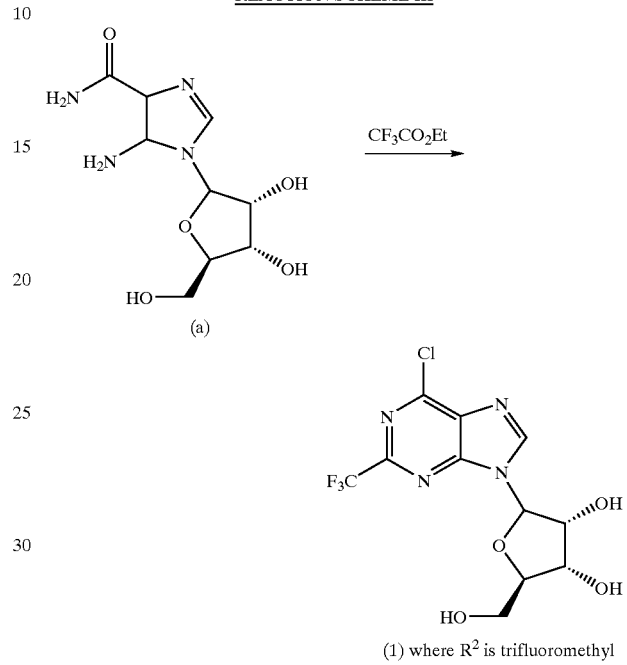

The preparation of a compound of formula (4) in which $R^2$ is nitrile is prepared as shown in Reaction Scheme IV.

REACTION SCHEME IV

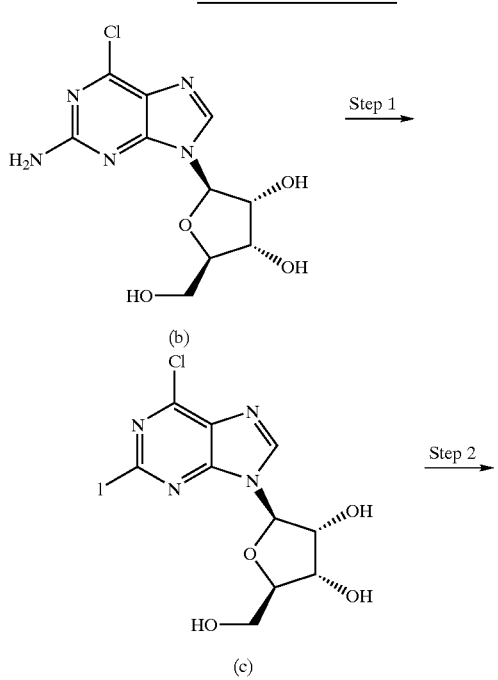

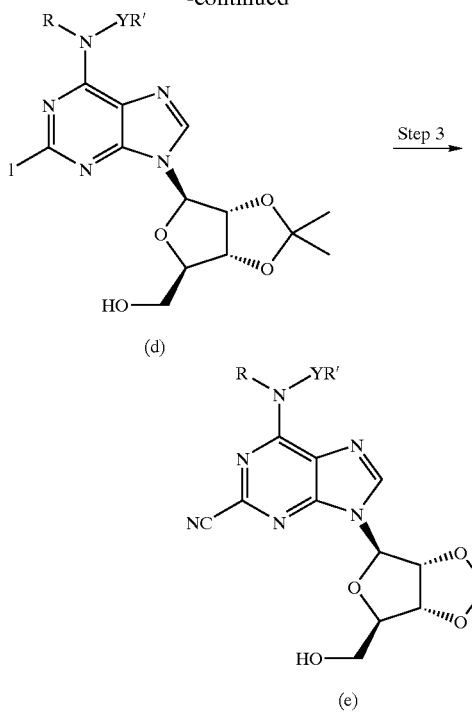

(d)

(e)

Starting Material of Formula (e)

The starting material of formula (b) is obtained commercially (Aldrich, Milwaukee). The product of formula (e) is converted into a compound of formula (4) as shown above.

The compounds of formula (1) where $R^2$ is acyl are obtained by reacting 2-stannyl-6-chloro-2',3',5'-tris-t-butyldimethylsilyladenosine (K. Kato et. al. J. Org. Chem. 1997, 62, 6833–6841) with an acid chloride.

Utility, Testing and Administration

General Utility

The compounds of Formula I are effective in the treatment of conditions known to respond to administration of a partial or full agonist of an $A_1$ adenosine receptor. Such conditions include, but are not limited to, acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter, congestive heart failure, non-insulin-dependent diabetes mellitus, hyperglycemia, epilepsy (anticonvulsant activity), and neuroprotection. $A_1$ agonists also have antilipolytic effects in adipocytes that leads to a decreased release of nonesterified fatty acids Testing Activity testing is conducted as described in those patents and literature citations referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

A. Preparation of a Compound of Formula (2) in which $R^3$ is Hydrogen

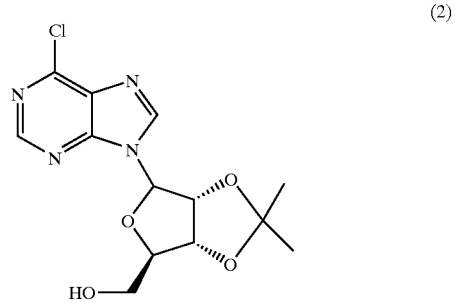

(2)

To a solution of 2-(6-chloropurin-9-yl)-5-hydroxymethyltetrahydrofuran-3,4-diol (a compound of formula (1)) (4.9 g, 17.1 mmol) and 2,2-dimethoxypropane (10.5 mL, 84.7 mmol) in dimethylformamide (100 mL) was added p-toluenesulfonic acid (325 mg, 1.71 mmol). After stirring for 24 hours at 70° C., the reaction was concentrated in vacuo and the residue purified by flash column chromatography (70% EtOAc/Hexanes) to give 6-(6-chloropurine-9-yl)-2,2-dimethyltetrahydrofuro[3,4-d][1,3]dioxol-4-yl]methanol, a compound of formula (2), as an off-white solid (2). (3.8 g, 68%) $^1$H NMR (CDCl3) δ 1.4 (s, 3H), 1.65 (s, 3H), 3.8–4.0 (dd, 2H), 4.6 (s, 1H), 5.1–5.3 (m, 2H), 6.0 (d, 1H), 8.25 (s, 1H), 8.8 (s, 1H).

B. Preparation of a Compound of Formula (2), Varying $R^2$

Similarly, following the procedure of 1A above, but replacing 2-(6-chloropurin-9-yl)-5-hydroxymethyltetrahydrofuran-3,4-diol with other compounds of formula (1), other compounds of formula (2) are prepared.

EXAMPLE 2

Preparation of a Compound of Formula (3)

A. Preparation of a Compound of Formula (3) in which $R^2$ is Hydrogen, $R^3$ is 2-Fluorophenyl, and X is a Covalent Bond

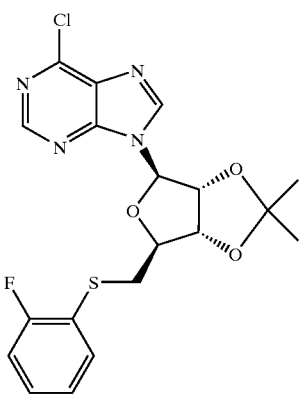

(3)

To a solution of 6-(6-chloropurine-9-yl)-2,2-dimethyltetrahydrofuro[3,4-d][1,3]dioxol-4-yl]methanol, a compound of formula (2) (0.48 g, 1.47 mmoles) in 20 mL of tetrahydrofuran was added triphenylphosphine (0.77 g, 2.94 mmoles) and diethylazodicarboxylate (0.47 mL, 2.94 mmoles), and the mixture stirred for 5 minutes. 2-Fluorothiophenol (0.31 mL, 2.94 mmoles) was then added, and the mixture was stirred under reflux. After 72 hours of reflux, the reaction was concentrated in vacuo and the residue purified by flash column chromatography (20% EtOAc/Hexanes) to give 1-{[(2S,1R,4R,5R)-4-(6-chloropurin-9-yl)-7,7-dimethyl-3,6,8-trioxabicyclo[3.3.0]oct-2-yl]methylthio}-2-fluorobenzene, a compound of formula (3), as a clear viscous oil (3). (0.25 g, ~40%) $^1$H NMR (CDCl3) δ 1.4 (s, 3H), 1.6 (s, 3H), 3.2 (m, 2H), 4.6 (t, 1H), 5.1 (m, 1H), 5.5 (m, 1H), 6.0 (d, 1H), 7.0 (m, 2H), 7.2 (m, 1H), 7.4 (m, 1H), 8.25 (s, 1H), 8.75 (s, 1H).

B. Preparation of a Compound of Formula (3), Varying $R^2$ and $R^3$

Similarly, following the procedure of 2A above, but optionally replacing 6-(6-chloropurine-9-yl)-2,2-dimethyltetrahydrofuro[3,4-d][1,3]dioxol-4-yl]methanol with other compounds of formula (2), and optionally replacing 2-fluorothiophenol with other compounds of formula $R^3$XH, the following compounds of formula (3) were prepared.

1-{[(2S,1R,4R,5R)-4-(6-chloropurin-9-yl)-7,7-dimethyl-3,6,8-trioxabicyclo[3.3.0]oct-2-yl]methylthio}benzene;

1-{[(2S,1R,4R,5R)-4-(6-chloropurin-9-yl)-7,7-dimethyl-3,6,8-trioxabicyclo[3.3.0]oct-2-yl]methylthio}-2,6-dichlorobenzene;

1-{[(2S,1R,4R,5R)-4-(6-chloropurin-9-yl)-7,7-dimethyl-3,6,8-trioxabicyclo[3.3.0]oct-2-yl]methylthio}-2,4-difluorobenzene;

1-{[(2S,1R,4R,5R)-4-(6-chloropurin-9-yl)-7,7-dimethyl-3,6,8-trioxabicyclo[3.3.0]oct-2-yl]methylthio}-4-fluorobenzene;

2-{[(2S,1R,4R,5R)-4-(6-chloropurin-9-yl)-7,7-dimethyl-3,6,8-trioxabicyclo[3.3.0]oct-2-yl]methylthio}-4-methyl-1,3-thiazole;

2-{[(2S,1R,4R,5R)-4-(6-chloropurin-9-yl)-7,7-dimethyl-3,6,8-trioxabicyclo[3.3.0]oct-2-yl]methylthio}-1,3-benzoxazole;

1-{[(2S,1R,4R,5R)-4-(6-chloropurin-9-yl)-7,7-dimethyl-3,6,8-trioxabicyclo[3.3.0]oct-2-yl]methylthio}-2-methylbenzene;

1-{[(2S,1R,4R,5R)-4-(6-chloropurin-9-yl)-7,7-dimethyl-3,6,8-trioxabicyclo[3.3.0]oct-2-yl]methylthio}-2-chlorobenzene;

1-{[(2S,1R,4R,5R)-4-(6-chloropurin-9-yl)-7,7-dimethyl-3,6,8-trioxabicyclo[3.3.0]oct-2-yl]methylthio}-4-chlorobenzene;

1-{[(2S,1R,4R,5R)-4-(6-chloropurin-9-yl)-7,7-dimethyl-3,6,8-trioxabicyclo[3.3.0]oct-2-yl]methylthio}-2-fluorobenzene;

1-{[(2S,1R,4R,5R)-4-(6-chloropurin-9-yl)-7,7-dimethyl-3,6,8-trioxabicyclo[3.3.0]oct-2-yl]methylthio}-3-fluorobenzene;

1-{[(2S,1R,4R,5R)-4-(6-chloropurin-9-yl)-7,7-dimethyl-3,6,8-trioxabicyclo[3.3.0]oct-2-yl]methylthio}-2-thiophene; and 1-{[(2S,1R,4R,5R)-4-(6-chloropurin-9-yl)-7,7-dimethyl-3,6,8-trioxabicyclo[3.3.0]oct-2-yl]methoxy}-2-fluorobenzene.

B. Preparation of a Compound of Formula (3), Varying $R^2$ and $R^3$

Similarly, following the procedure of 2A above, but optionally replacing 6-(6-chloropurine-9-yl)-2,2-dimethyltetrahydrofuro[3,4-d][1,3]dioxol-4-yl]methanol with other compounds of formula (2), and optionally replacing 2-fluorothiophenol with other compounds of formula $R^3$XH, other compounds of formula (3) are prepared.

EXAMPLE 3

Preparation of a Compound of Formula (4)

A. Preparation of a Compound of Formula (4) in which R is Hydrogen $R^1$ is Cyclopentyl, $R^2$ is Hydrogen, $R^3$ is 2-Fluorophenyl, and X and Y are Covalent Bonds

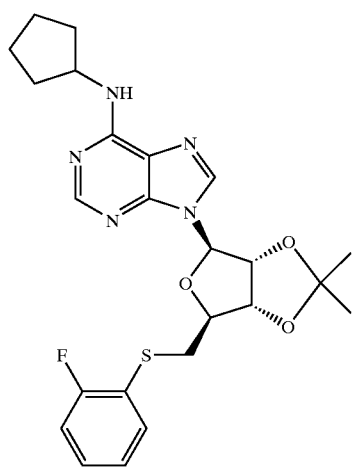

(4)

To a solution of 1-{[(2S,1R,4R,5R)-4-(6-chloropurin-9-yl)-7,7-dimethyl-3,6,8-trioxabicyclo[3.3.0]oct-2-yl] methylthio}-2-fluorobenzene, a compound of formula (3), (0.125 g, 2.86 mmoles) in 10 mL of ethanol and 1 mL of triethylamine was added cyclopentylamine in excess, and the mixture refluxed under nitrogen for 24 hours. The solvent was removed under reduced pressure, and the residue was purified by preparative TLC using 1:1 EtOAc:Hexanes to give (9-{(4S,1R,2R,5R)-4-[(2-fluorophenylthio)methyl]-7,7-dimethyl-3,6,8-trioxabicyclo[3.3.0]oct-2-yl}purin-6-yl)cyclopentylamine, a compound of formula (4), as a yellow oil (80 mg, 56%) $^1$H NMR (CDCl3) δ 1.4 (s, 3H), 1.6 (s, 3H), 1.6–2.4 (m, 6H), 3.15–3.25 (m, 2H), 4.1 (bs, 1H), 4.4 (t, 1H), 5.1 (m, 1H), 5.5 (m, 1H), 6.0 (d, 1H), 6.2 (bs, 1H), 7.0 (m, 2H), 7.2 (m, 1H), 7.4 (m, 1H), 7.8 (s, 1H), 8.25 (s, 1H).

B. Preparation of a Compound of Formula (4), Varying $R^1$, $R^2$ $R^3$, and Y

Similarly, following the procedure of 3A above, but optionally replacing 1-{[(2S,1R,4R,5R)-4-(6-chloropurin-9-yl)-7,7-dimethyl-3,6,8-trioxabicyclo[3.3.0]oct-2-yl]methylthio}-2-fluorobenzene with other compounds of formula (3), and optionally replacing cyclopentylamine with other compounds of formula $R^1YNH_2$, the following compounds of formula (4) in which R is methyl, $R^1$ is 2-(3,4-dimethoxyphenyl)ethyl, $R^2$ is hydrogen, and X and Y are covalent bonds were also prepared:
$R^3$ is 2,6-dichlorophenyl;
$R^3$ is 4-methylthiazol-2-yl;
$R^3$ is 1,3-benzoxazol-2-yl;
2-methylphenyl;
$R^3$ is 2-chlorophenyl; and
$R^3$ is 4-chlorophenyl.

C. Preparation of a Compound of Formula (4), Varying $R^1$, $R^2$ $R^3$, and Y

Similarly, following the procedure of 3A above, but optionally replacing 1-{[(2S,1R,4R,5R)-4-(6-chloropurin-9-yl)-7,7-dimethyl-3,6,8-trioxabicyclo[3.30]oct-2-yl]methylthio}-2-fluorobenzene with other compounds of formula (3), and optionally replacing cyclopentylamine with other compounds of formula $R^1YNH_2$, other compounds of formula (4) are prepared.

EXAMPLE 4

Preparation of a Compound of Formula I
A. Preparation of a Compound of Formula I in which R is Hydrogen, $R^1$ is Cyclopentyl, $R^2$ is Hydrogen, $R^3$ is 2-Fluorophenyl, and X and Y are Covalent Bonds

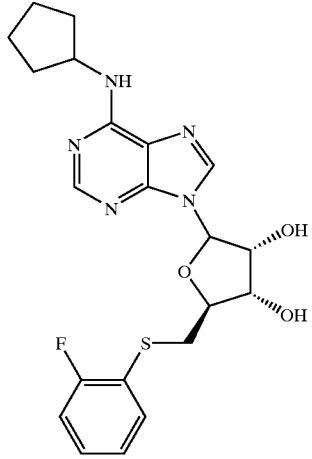

Formula I (9-{(4S,1R,2R,5R)-4-[(2-fluorophenylthio)methyl]-7,7-dimethyl-3,6,8-trioxabicyclo[3.3.0]oct-2-yl}purin-6-yl)cyclopentylamine, a compound of formula (4) (50 mg) was dissolved in a mixture of acetic acid (8 mL) and water (2 mL) and heated at 90° C. for 16 hours. Solvents were removed under reduced pressure, and the residue was purified by preparative TLC [methanol-dichloromethane(1:9)] to afford (4S,5S,3R)-2-[6-(cyclopentylamino)purin-9-yl]-5-[(2-fluorophenylthio)methyl]oxolane-3,4-diol, a compound of Formula I,. $^1$H NMR (CDCl3) δ 1.6–2.4 (m, 6H), 3.15–3.25 (m, 2H), 4.1 (bs, 1H), 4.4–4.65 (m, 4H), 6.0 (d, 1H), 6.8 (bs, 1H), 7.05 (m, 2H), 7.2 (m, 1H), 7.4 (m, 1H), 7.8 (s, 1H), 8.25 (s, 1H).

B. Preparation of a Compound of Formula I, Varying $R^1$

Similarly, following the procedure of 4A above, but replacing (9-{(4S,1R,2R,5R)-4-[(2-fluorophenylthio)methyl]-7,7-dimethyl-3,6,8-trioxabicyclo[3.3.0]oct-2-yl}purin-6-yl)cyclopentylamine with other compounds of formula (4), the following compounds of Formula I were made, in which R, $R^2$, $R^4$ and $R^5$ are hydrogen, $R^3$ is 2-fluorophenyl, X and Y are covalent bonds, and $R^1$ is:
cyclopentyl;
(R,R)-2-hydroxycyclopentyl;
(R,S)-2-hydroxycyclopentyl;
bicyclo[2.2.1]heptan-2-yl,
7,7-dimethylbicyclo[2.2.1]heptan-2-yl;
bicyclo[2.2.1]heptan-2-yl-3-carboxylic acid ethyl ester;
bicyclo[2.2.1]heptan-2-yl-3-carboxylic acid
bicyclo[2.2.1]heptan-2-yl-3-methanol;
cyclopentyl-2-carboxylic acid ethyl ester;
cyclopentyl-2-carboxylic acid;
(R) 2-hydroxycyclohexyl;
(S) 2-hydroxycyclohexyl;
(R)-1-phenylethyl;
(S)-1-phenylethyl;
(4-fluorophenyl)methyl;
4-trifluoromethoxyphenylmethyl;
2,6-difluorophenylmethyl;
(3-methoxyphenyl)methyl;
(4-methoxyphenyl)methyl;
2-benzyloxycyclopentyl;
(4-methylphenyl)ethyl;
furan-2-yl;
phenylcyclopropyl;
3-propionic acid ethyl ester;
cyclohexyl;
1-(4-methoxyphenyl)ethyl;
3-trifluoromethylphenylmethyl;
3,5-dichlorophenylmethyl;
(3-fluorophenyl)methyl;
(2-trifluoromethylphenyl)methyl;
(4-chlorophenyl)methyl;
(2-fluorophenyl)methyl;
2-chloro-4-fluorophenylmethyl;
2-fluoro-4-trifluoromethylphenylmethyl;
2,4-dichlorophenylethyl;
(R)-2-phenylpropyl;
(S)-2-phenylpropyl;
2-(3-fluorophenyl)ethyl;
2-(2-chlorophenyl)ethyl;
6,6-dimethylbicyclo[3.3.1]hept-3-yl;
4-(tert-butyl)cyclohexyl;
2-chlorophenylmethyl;
1-(4-methylphenyl)ethyl;
(3-methylphenyl)methyl;
(4-methylphenyl)methyl;
2-trifluoromethyl-5-fluorophenylmethyl;
2-chloro-3-trifluoromethylphenylmethyl;
2,6,6-trimethylbicyclo[3.3.1]hept-3-yl;
1-naphtylmethyl;

bicyclo[3.1.1]heptyl-3-yl;
2-isopropyl-4-methylcyclohexyl;
2-carboxamidocyclohexyl;
(R)-2-carboxycyclohexyl;
(S)-2-carboxycyclohexyl;
2-hydroxymethylcyclohexyl;
2-carboxycyclohexyl ethyl ester;
2-carboxy-4-phenylcyclohexyl;
2-carboxybicyclo[2.2.1]hept-5-en-3-yl; and
2-carboxybicyclo[2.2.1]hept-3-yl ethyl ester.

Similarly, the following compounds of Formula I where R, $R^2$, $R^4$ and $R^5$ are hydrogen, and X and Y are covalent bonds were prepared:

$R^3$ is 4-fluorophenyl and $R^1$ is cyclopentyl;
$R^3$ is 2-methylphenyl and $R^1$ is cyclopentyl; and
$R^3$ is 2,4-difluorophenyl and $R^1$ is cyclopentyl.

C. Preparation of a Compound of Formula I, Varying $R^1$, $R^2$ $R^3$, $R^4$, $R^5$, X and Y Similarly, following the procedure of 4A above, or using the combinatorial synthesis of Examples 5–8, but optionally replacing (9-{(4S,1R,2R,5R)-4-[(2-fluorophenylthio) methyl]-7,7-dimethyl-3,6,8-trioxabicyclo[3.3.0]oct-2-yl}purin-6-yl)cyclopentylamine with other compounds of formula (4), the following compounds of Formula I were made.

| $R^3$ | $R^1$ |
|---|---|
| 2,6 dichlorophenyl | 1-benzylpyrrolidin-3-yl |
| 2,6 dichlorophenyl | 1-benzylpiperidin-4-yl |
| 2,4 difluorophenyl | 1-benzylpyrrolidin-3-yl |
| 4-fluorophenyl | 1-benzylpiperidin-4-yl |
| 4-methyl-1,3-thiazole-2-yl | 1-benzylpyrrolidin-3-yl |
| 4-methyl-1,3-thiazole-2-yl | 1-benzylpiperidin-4-yl |
| 1,3-benzoxazol-2-yl | 1-benzylpyrrolidin-3-yl |
| 2-methylbenzyl | 1-benzylpyrrolidin-3-yl |
| 2-methylphenyl | 1-benzylpiperidin-4-yl |
| 2-chlorophenyl | 1-benzylpyrrolidin-3-yl |
| 2-chlorophenyl | 1-benzylpiperidin-4-yl |
| 2-fluorophenyl | 1-benzylpyrrolidin-3-yl |
| thiophen-2-yl | 1-benzylpyrrolidin-3-yl |
| 2,6 dichlorophenyl | ethyl |
| 2,6 dichlorophenyl | but-1-yl |
| 2,6 dichlorophenyl | isobut-1-yl |
| 2,6 dichlorophenyl | t-butyl |
| 2,6 dichlorophenyl | pent-3-yl |
| 2,6 dichlorophenyl | cyclobutyl |
| 2,6 dichlorophenyl | cyclopentyl |
| 2,6 dichlorophenyl | cyclohexyl |
| 2,6 dichlorophenyl | cycloheptyl |
| 2,6 dichlorophenyl | cyclooctyl |
| 2,6 dichlorophenyl | (R) bicyclo[2.2.1]heptan-2-yl |
| 2,6-dichlorophenyl | 3-(pyrrolid-2-one-1-yl)propyl |
| 2,6 dichlorophenyl | tetrahydrofuran-2-yl-methyl |
| 2,6 dichlorophenyl | benzyl |
| 2,6 dichlorophenyl | (2-methylphenyl)methyl |
| 2,6 dichlorophenyl | (4-methylphenyl)methyl |
| 2,6 dichlorophenyl | 1-phenylethyl |
| 2,6 dichlorophenyl | (2-methoxyphenyl)methyl |
| 2,6 dichlorophenyl | (4-methoxyphenyl)methyl |
| 2,6 dichlorophenyl | 1-cyclohexylethyl |
| 2,6 dichlorophenyl | 3-fluorobenzyl |
| 2,6-dichlorophenyl | 4-fluorobenzyl |
| 2,6 dichlorophenyl | (2-trifluoromethylphenyl)methyl |
| 2,6 dichlorophenyl | (2-fluoro-6-chlorophenyl)methyl |
| 2,6-dichlorophenyl | 2-(3-methoxyphenyl)ethyl |
| 2,6-dichlorophenyl | 2-(4-methoxyphenyl)ethyl |
| 2,6 dichlorophenyl | 2-(3-fluorophenyl)ethyl |
| 2,6 dichlorophenyl | 2-(4-fluorophenyl)ethyl |
| 2,6 dichlorophenyl | 2-(3-chlorophenyl)ethyl |
| 2,6 dichlorophenyl | 2,2-bis-phenylethyl |
| 2,6 dichlorophenyl | 2-(thiophen-2-yl)ethyl |
| 2,6 dichlorophenyl | 3-dimethylaminopropyl |
| 2,6 dichlorophenyl | 2-(morpholin-4-yl)ethyl |
| 2,6 dichlorophenyl | 2-[N-ethyl-N-(3-methylphenyl)amino]ethyl |
| 2,6-dichlorophenyl | pyridin-3-ylmethyl |
| 2,6-dichlorophenyl | 3-(imidazol-1-yl)propyl |
| 2,6-dichlorophenyl | 1,2-dimethylpropyl |
| 2,6 dichlorophenyl | (3,4-methylenedioxyphenyl)methyl |
| 2,6-dichlorophenyl | (R) bicyclo[2.2.1]heptan-2-yl |
| 2,6-dichlorophenyl | 4-methoxyphenyl |
| 2,4-dichlorophenyl | 4-ethoxyphenyl |
| 2,4-dichlorophenyl | 2-indanyl |
| 2,4-dichlorophenyl | 2-fluorophenyl |
| 2,4-difluorophenyl | ethyl |
| 2,4-difluorophenyl | but-1-yl |
| 2,4-difluorophenyl | 2-methylprop-1-yl |
| 2,4-difluorophenyl | pent-3-yl |
| 2,4-difluorophenyl | cyclopropylmethyl |
| 2,4-difluorophenyl | cyclobutyl |
| 2,4-difluorophenyl | cyclopentyl |
| 2,4-difluorophenyl | cyclohexyl |
| 2,4-difluorophenyl | cycloheptyl |
| 2,4-difluorophenyl | cyclooctyl |
| 2,4-difluorophenyl | (R) bicyclo[2.2.1]heptan-2-yl |
| 2,4-difluorophenyl | 2,6,6-trimethylbicyclo[3.1.1]hept-3-yl |
| 2,4-difluorophenyl | 2-(cyclohex-1-en-1-yl)ethyl |
| 2,4-difluorophenyl | 3-(2-oxopyrrolidin-1-yl)propyl |
| 2,4-difluorophenyl | tetrahydrofuran-2-yl-methyl |
| 2,4-difluorophenyl | 2-ethylhex-1-yl |
| 2,4-difluorophenyl | (2-methylphenyl)methyl |
| 2,4-difluorophenyl | 1-phenylethyl |
| 2,4-difluorophenyl | (2-methoxyphenyl)methyl |
| 2,4-difluorophenyl | (3-methoxyphenyl)methyl |
| 2,4-difluorophenyl | (4-methoxyphenyl)methyl |
| 2,4-difluorophenyl | (R)-1-cyclohexylethyl |
| 2,4-difluorophenyl | (S)-1-cyclohexylethyl |
| 2,4-difluorophenyl | (2-fluorophenyl)methyl |
| 2,4-difluorophenyl | (3-fluorophenyl)methyl |
| 2,4-difluorophenyl | (4-fluorophenyl)methyl |
| 2,4-difluorophenyl | (4-chlorophenyl)methyl |
| 2,4-difluorophenyl | 2-phenylethyl |
| 2,4-difluorophenyl | (2,4-dimethoxyphenyl)methyl |
| 2,4-difluorophenyl | 2-(3-fluorophenyl)ethyl |
| 2,4-difluorophenyl | 2-(4-fluorophenyl)ethyl |
| 2,4-difluorophenyl | 2-(3-chlorophenyl)ethyl |
| 2,4-difluorophenyl | 2-(2,2-bisphenyl)ethyl |
| 2,4-difluorophenyl | 3-phenylpropyl |
| 2,4-difluorophenyl | 2-(thiophen-2-yl)ethyl |
| 2,4-difluorophenyl | 3,3-bisphenylpropyl |
| 2,4-difluorophenyl | 2,2-dimethyl-3-(dimethylamino)propyl |
| 2,4-difluorophenyl | pyridin-2-yl-methyl |
| 2,4-difluorophenyl | pyridin-3-yl-methyl |
| 2,4-difluorophenyl | 3-(imidazol-1-yl)propyl |
| 2,4-difluorophenyl | (3,4-methylenedioxyphenyl)methyl |
| 2,4-difluorophenyl | (R) bicyclo[2.2.1]heptan-2-yl |
| 2,4-difluorophenyl | phenyl |
| 2,4-difluorophenyl | 4-methoxyphenyl |
| 2,4-difluorophenyl | 4-phenoxyphenyl |
| 2,4-difluorophenyl | 2-fluorophenyl |
| 2,4-difluorophenyl | 4-chlorophenyl |
| 4-fluorophenyl | but-1-yl |
| 4-fluorophenyl | sec butyl-1-yl |
| 4-fluorophenyl | t-butyl |
| 4-fluorophenyl | pent-3-yl |
| 4-fluorophenyl | cyclopropylmethyl |
| 4-fluorophenyl | cyclobutyl |
| 4-fluorophenyl | cyclopentyl |
| 4-fluorophenyl | cyclohexyl |
| 4-fluorophenyl | cycloheptyl |
| 4-fluorophenyl | cyclooctyl |
| 4-fluorophenyl | 3,3,5-trimethylcyclohexyl |
| 4-fluorophenyl | (R) bicyclo[2.2.1]heptan-2-yl |
| 4-fluorophenyl | 2,6,6-trimethylbicyclo[3.1.1]heptanyl |
| 4-fluorophenyl | 2-(cyclohex-1-en-1-yl)ethyl |
| 4-fluorophenyl | 2-ethylhex-3-yl |
| 4-fluorophenyl | phenyl |
| 4-fluorophenyl | (2-methylphenyl)methyl |
| 4-fluorophenyl | (3-methoxyphenyl)methyl |
| 4-fluorophenyl | 1-cyclohexylethyl |
| 4-fluorophenyl | (4-fluorophenyl)methyl |
| 4-fluorophenyl | (4-chlorophenyl)methyl |

-continued

| | |
|---|---|
| 4-fluorophenyl | (2-trifluoromethylphenyl)methyl |
| 4-fluorophenyl | 2-phenylethyl |
| 4-fluorophenyl | 2-(3-methoxyphenyl)ethyl |
| 4-fluorophenyl | 2-(4-methoxyphenyl)ethyl |
| 4-fluorophenyl | 2-(3-fluorophenyl)ethyl |
| 4-fluorophenyl | 2-(3-chlorophenyl)ethyl |
| 4-fluorophenyl | 3-phenylpropyl |
| 4-fluorophenyl | thiophen-2-ylmethyl |
| 4-fluorophenyl | 2,2-dimethyl-3-(dimethylamino)propyl |
| 4-fluorophenyl | 2-(morpholin-4-yl)ethyl- |
| 4-fluorophenyl | 2-[N-ethyl-N-(3-methylphenyl)]aminoethyl |
| 4-fluorophenyl | pyridin-2-yl-methyl |
| 4-fluorophenyl | pyridin-3-ylmethyl |
| 4-fluorophenyl | pyridin-4-yl-methyl |
| 4-fluorophenyl | 3-(imidazol-1-yl)propyl |
| 4-fluorophenyl | (3,4-methylenedioxyphenyl)methyl |
| 4-fluorophenyl | R) bicyclo[2.2.1]heptanyl |
| 4-fluorophenyl | phenyl |
| 4-fluorophenyl | 4-methoxyphenyl |
| 4-fluorophenyl | 4-ethoxyphenyl |
| 4-fluorophenyl | 4-phenoxyphenyl |
| 4-methyl-1,3-thiazole | ethyl |
| 4-methyl-1,3-thiazole | but-1-yl |
| 4-methyl-1,3-thiazole | sec but-1-yl |
| 4-methyl-1,3-thiazole | t-butyl |
| 4-methyl-1,3-thiazole | pent-3-yl |
| 4-methyl-1,3-thiazole | cyclopropylmethyl |
| 4-methyl-1,3-thiazole | cyclobutyl |
| 4-methyl-1,3-thiazole | cyclopentyl |
| 4-methyl-1,3-thiazole | cyclohexyl |
| 4-methyl-1,3-thiazole | cycloheptyl |
| 4-methyl-1,3-thiazole | 3,3,5 trimethylcyclohexyl |
| 4-methyl-1,3-thiazole | (R) bicyclo[2.2.1]heptan-2-yl |
| 4-methyl-1,3-thiazole | 2-(cyclohex-1-en-1-yl)ethyl |
| 4-methyl-1,3-thiazole | 3-(2-oxopyrrolidin-1-yl)propyl |
| 4-methyl-1,3-thiazole | phenyl |
| 4-methyl-1,3-thiazole | (2-methylphenyl)methyl |
| 4-methyl-1,3-thiazole | (3-methylphenyl)methyl |
| 4-methyl-1,3-thiazole | 1-phenylethyl |
| 4-methyl-1,3-thiazole | (3-methoxyphenyl)methyl |
| 4-methyl-1,3-thiazole | (4-methoxyphenyl)methyl |
| 4-methyl-1,3-thiazole | (2-fluorophenyl)methyl |
| 4-methyl-1,3-thiazole | (4-chlorophenyl)methyl |
| 4-methyl-1,3-thiazole | (2-trifluoromethylphenyl)methyl |
| 4-methyl-1,3-thiazole | (3,4-dichlorophenyl)methyl |
| 4-methyl-1,3-thiazole | 2-phenylethyl |
| 4-methyl-1,3-thiazole | 2-(3-methoxyphenyl)ethyl |
| 4-methyl-1,3-thiazole | (4-methoxyphenyl)methyl |
| 4-methyl-1,3-thiazole | 2-(3-fluorophenyl)ethyl |
| 4-methyl-1,3-thiazole | 2-(4-fluorophenyl)ethyl |
| 4-methyl-1,3-thiazole | 2-(2-chlorophenyl)ethyl |
| 4-methyl-1,3-thiazole | 2-(3-chlorophenyl)ethyl |
| 4-methyl-1,3-thiazole | 2,2-bisphenylethyl |
| 4-methyl-1,3-thiazole | 2-(thiophen-2-yl)ethyl |
| 4-methyl-1,3-thiazole | 3,3-bisphenylpropyl |
| 4-methyl-1,3-thiazole | 4-phenylbut-2-yl |
| 4-methyl-1,3-thiazole | 3-(dimethylamino)propyl |
| 4-methyl-1,3-thiazole | 2-(morpholin-4-yl)ethyl- |
| 4-methyl-1,3-thiazole | 2-[2-ethyl-2-(3-methylphenyl)amino]ethyl |
| 4-methyl-1,3-thiazole | pyridin-3-ylmethyl |
| 4-methyl-1,3-thiazole | pyridin-4-ylmethyl |
| 4-methyl-1,3-thiazole | 3-(imidazol-1-yl)propyl |
| 4-methyl-1,3-thiazole | 3-methylbut-2-yl |
| 4-methyl-1,3-thiazole | (3,4-methylenedioxyphenyl)methyl |
| 4-methyl-1,3-thiazole | (S) bicyclo[2.2.1]heptan-2-yl |
| 4-methyl-1,3-thiazole | phenyl |
| 1,3-benzoxazol-2-yl | pent-3-yl |
| 1,3-benzoxazol-2-yl | cyclopropylmethyl |
| 1,3-benzoxazol-2-yl | cyclopentyl |
| 1,3-benzoxazol-2-yl | cycloheptyl |
| 1,3-benzoxazol-2-yl | cyclooctyl |
| 1,3-benzoxazol-2-yl | 3,3,5-trimethylcyclohexyl |
| 1,3-benzoxazol-2-yl | 3-(2-oxopyrrolidin-1-yl)propyl |
| 1,3-benzoxazol-2-yl | tetrahydrofuran-2-yl-methyl |
| 1,3-benzoxazol-2-yl | 2-ethylhex-1-yl |
| 1,3-benzoxazol-2-yl | phenyl |
| 1,3-benzoxazol-2-yl | (2-methylphenyl)methyl |
| 1,3-benzoxazol-2-yl | (4-methylphenyl)methyl |
| 1,3-benzoxazol-2-yl | 1-phenylethyl |
| 1,3-benzoxazol-2-yl | (2-methoxyphenyl)methyl |
| 1,3-benzoxazol-2-yl | (3-methoxyphenyl)methyl |
| 1,3-benzoxazol-2-yl | (4-methoxyphenyl)methyl |
| 1,3-benzoxazol-2-yl | 1-cyclohexylethyl |
| 1,3-benzoxazol-2-yl | (3-fluorophenyl)methyl |
| 1,3-benzoxazol-2-yl | (4-fluorophenyl)methyl |
| 1,3-benzoxazol-2-yl | (2-fluoro-6-chlorophenyl)methyl |
| 1,3-benzoxazol-2-yl | (2,4-dichlorophenyl)methyl |
| 1,3-benzoxazol-2-yl | 2-phenylethyl |
| 1,3-benzoxazol-2-yl | 2-(3-methoxyphenyl)ethyl |
| 1,3-benzoxazol-2-yl | 2-(4-methoxyhenyl)ethyl |
| 1,3-benzoxazol-2-yl | 2-(4-fluorophenyl)ethyl |
| 1,3-benzoxazol-2-yl | 2-(2-chlorophenyl)ethyl |
| 1,3-benzoxazol-2-yl | 2-(3-chlorophenyl)ethyl |
| 1,3-benzoxazol-2-yl | 2,2-bis-phenylethyl |
| 1,3-benzoxazol-2-yl | 3-phenylpropyl |
| 1,3-benzoxazol-2-yl | 2-(thiophen-2-yl)ethyl |
| 1,3-benzoxazol-2-yl | 3,3-bisphenylpropyl |
| 1,3-benzoxazol-2-yl | 2-(morpholin-4-yl)ethyl- |
| 1,3-benzoxazol-2-yl | 2-[N-ethyl-N-(3-methylphenyl)amino]ethyl |
| 1,3-benzoxazol-2-yl | 3-methylbut-2-yl |
| 1,3-benzoxazol-2-yl | (S) bicyclo[2.2.1]heptan-2-yl |
| 1,3-benzoxazol-2-yl | phenyl |
| 1,3-benzoxazol-2-yl | 4-ethoxyphenyl |
| 1,3-benzoxazol-2-yl | 2-indanyl |
| 2-methylphenyl | ethyl |
| 2-methylphenyl | but-1-yl |
| 2-methylphenyl | sec-but-1-yl |
| 2-methylphenyl | pent-3-yl |
| 2-methylphenyl | cyclopropylmethyl |
| 2-methylphenyl | cyclopentyl |
| 2-methylphenyl | cycloheptyl |
| 2-methylphenyl | 3,3,5-trimethylcyclohexyl |
| 2-methylphenyl | (S) bicyclo[2.2.1]heptan-2-yl |
| 2-methylphenyl | 2,6,6-trimethylbicyclo[3.1.1]hept-3-yl |
| 2-methylphenyl | 2-(cyclohex-1-en-1-yl)ethyl |
| 2-methylphenyl | 3-(pyrrolid-2-one-1-yl)propyl |
| 2-methylphenyl | 2-ethylhex-1-yl |
| 2-methylphenyl | (2-methylphenyl)methyl |
| 2-methylphenyl | (3-methylphenyl)methyl |
| 2-methylphenyl | 1-phenylethyl |
| 2-methylphenyl | (4-methoxyphenyl)methyl |
| 2-methylphenyl | (R)-1-cyclohexylethyl |
| 2-methylphenyl | (2-trifluoromethylphenyl)methyl |
| 2-methylphenyl | (3,4-dichlorophenyl)methyl |
| 2-methylphenyl | 2-(3-fluorophenyl)ethyl |
| 2-methylphenyl | 2-(4-fluorophenyl)ethyl |
| 2-methylphenyl | 2-(2-chlorophenyl)ethyl |
| 2-methylphenyl | 2-(3-chlorophenyl)ethyl |
| 2-methylphenyl | 3-phenylpropyl |
| 2-methylphenyl | 2,2-bisphenylethyl |
| 2-methylphenyl | 3-dimethylaminopropyl |
| 2-methylphenyl | 2-(morpholin-4-yl)ethyl- |
| 2-methylphenyl | 2-[N-ethyl-N-(3-methylphenyl)amino]ethyl |
| 2-methylphenyl | pyridin-2-yl-methyl |
| 2-methylphenyl | pyridin-3-ylmethyl |
| 2-methylphenyl | pyridin-4-yl-methyl |
| 2-methylphenyl | 3-propylimidazol-1-yl |
| 2-methylphenyl | 3,4-methylenedioxyphenylmethyl |
| 2-methylphenyl | (R) bicyclo[2.2.1]heptan-2-yl |
| 2-methylphenyl | 4-methoxyphenyl |
| 2-methylphenyl | 4-phenoxyphenyl |
| 2-methylphenyl | 2-indanyl |
| 2-chlorophenyl | ethyl |
| 2-chlorophenyl | but-1-yl |
| 2-chlorophenyl | pent-3-yl |
| 2-chlorophenyl | cyclopropylmethyl |
| 2-chlorophenyl | cyclopentyl |
| 2-chlorophenyl | cyclohexyl |
| 2-chlorophenyl | cycloheptyl |
| 2-chlorophenyl | 3,3,5 trimethylhexyl |
| 2-chlorophenyl | 2-(cyclohex-1-en-1-yl)ethyl |
| 2-chlorophenyl | 3-(pyrrolid-2-one-1-yl)propyl |
| 2-chlorophenyl | tetrahydrofuran-2-ylmethyl |
| 2-chlorophenyl | 2-ethylhex-1-yl |
| 2-chlorophenyl | 2-(4-methoxypheny)ethyl |
| 2-chlorophenyl | 2-(3-fluorophenyl)ethyl |
| 2-chlorophenyl | 2-(4-fluorophenyl)ethyl |
| 2-chlorophenyl | 2-(2-chlorophenyl)ethyl |

-continued

| | |
|---|---|
| 2-chlorophenyl | 2-(3-chlorophenyl)ethyl |
| 2-chlorophenyl | 2,2 bisphenylethyl |
| 2-chlorophenyl | 3-phenylpropyl |
| 2-chlorophenyl | 2-(thiophen-2-yl)ethyl |
| 2-chlorophenyl | 3,3-bisphenylpropyl |
| 2-chlorophenyl | 4-phenylbut-2-yl |
| 2-chlorophenyl | 3-dimethylaminopropyl |
| 2-chlorophenyl | 2-(morpholin-4-yl)ethyl- |
| 2-chlorophenyl | 2-[N-ethyl-N-(3-methylphenyl)amino]ethyl |
| 2-chlorophenyl | pyridin-2-yl-methyl |
| 2-chlorophenyl | pyridin-4-yl-methyl |
| 2-chlorophenyl | 3-(imidazol-3-yl)propyls |
| 2-chlorophenyl | 1,2-dimethylpropyl |
| 2-chlorophenyl | pentyl-3-yl |
| 2-chlorophenyl | 3,4-methylenedioxyphenylmethyl |
| 2-chlorophenyl | (S) bicyclo[2.2.1]heptan-2-yl |
| 2-chlorophenyl | 4-methoxyphenyl |
| 2-chlorophenyl | 4-ethoxyphenyl |
| 2-chlorophenyl | 4-phenoxyphenyl |
| 2-chlorophenyl | 2-indanyl |
| 2-chlorophenyl | 4-chlorophenyl |
| 2-chlorophenyl | tetrahydropyran-4-yl |
| 2-chlorophenyl | phenylmethyl |
| 2-chlorophenyl | (2-methylphenyl)methyl |
| 2-chlorophenyl | (3-methylphenyl)methyl |
| 2-chlorophenyl | 1-phenylethyl |
| 2-chlorophenyl | (2-methoxyphenyl)methyl |
| 2-chlorophenyl | (3-methoxyphenyl)methyl |
| 2-chlorophenyl | (4-methoxyphenyl)methyl |
| 2-chlorophenyl | 1-(cyclohexyl)ethyl |
| 2-chlorophenyl | (3-fluorophenyl)methyl |
| 2-chlorophenyl | (3-chlorophenyl)methyl |
| 2-chlorophenyl | (2-trifluoromethylphenyl)methyl |
| 2-chlorophenyl | (2-fluoro-6-chlorophenyl)methyl |
| 2-chlorophenyl | 2-phenylethyl |
| 2-chlorophenyl | 2-(3-methoxyphenyl)ethyl |
| 2-chlorophenyl | ethyl |
| 4-chlorophenyl | isobut-1-yl |
| 4-chlorophenyl | t-butyl |
| 4-chlorophenyl | pent-3-yl |
| 4-chlorophenyl | cyclopropylmethyl |
| 4-chlorophenyl | cyclopentyl |
| 4-chlorophenyl | cyclohexyl |
| 4-chlorophenyl | cycloheptyl |
| 4-chlorophenyl | 3,3,5 trimethylcyclohexyl |
| 4-chlorophenyl | (S) bicyclo[2.2.1]heptan-2-yl |
| 4-chlorophenyl | 2,6,6-trimethylbicyclo[3.1.1]hept-3-yl |
| 4-chlorophenyl | cyclohexylethyl |
| 4-chlorophenyl | tetrahydrofuran-2-yl-methyl |
| 4-chlorophenyl | 2-ethylhex-1-yl |
| 4-chlorophenyl | phenylmethyl |
| 4-chlorophenyl | (2-methylphenyl)methyl |
| 4-chlorophenyl | (3-methylphenyl)methyl |
| 4-chlorophenyl | (4-methylphenyl)methyl |
| 4-chlorophenyl | 2-phenylethyl |
| 4-chlorophenyl | (2-methoxyphenyl)methyl |
| 4-chlorophenyl | (3-methoxyphenyl)methyl |
| 4-chlorophenyl | (4-methoxyphenyl)methyl |
| 4-chlorophenyl | (R)-1-cyclohexlethyl |
| 4-chlorophenyl | (S)-1-cyclohexylethyl |
| 4-chlorophenyl | (2-fluorophenyl)methyl |
| 4-chlorophenyl | (3-fluorophenyl)methyl |
| 4-chlorophenyl | (4-chlorophenyl)methyl |
| 4-chlorophenyl | (2-fluoro-6-chlorophenyl)methyl |
| 4-chlorophenyl | (2,4-dichlorophenyl)methyl |
| 4-chlorophenyl | 2-phenylethyl |
| 4-chlorophenyl | 2-(3-methoxyhenyl)ethyl |
| 4-chlorophenyl | 2-(3-fluorophenyl)ethyl |
| 4-chlorophenyl | 2-(4-fluorophenyl)ethyl |
| 4-chlorophenyl | 2-(2-chlorophenyl)ethyl |
| 4-chlorophenyl | 2-(3-chlorophenyl)ethyl |
| 4-chlorophenyl | 2,2-bis-phenylethyl |
| 4-chlorophenyl | 3-phenylpropyl |
| 4-chlorophenyl | 2-(thiophene-2-yl)ethyl |
| 4-chlorophenyl | 3,3 bisphenylpropyl |
| 4-chlorophenyl | 4-phenylbut-2-yl |
| 4-chlorophenyl | N-ethyl-N-(3-methylphenyl)ethylamino |
| 4-chlorophenyl | phenyl |
| 4-chlorophenyl | 4-methoxyphenyl |
| 4-chlorophenyl | 4-ethoxyphenyl |
| 4-chlorophenyl | 4-phenoxyphenyl |
| 4-chlorophenyl | ethyl |
| 2-fluorophenyl | but-1-yl |
| 2-fluorophenyl | isobut-1-yl |
| 2-fluorophenyl | t-butyl |
| 2-fluorophenyl | pent-3-yl |
| 2-fluorophenyl | cyclopropylmethyl |
| 2-fluorophenyl | cyclobutyl |
| 2-fluorophenyl | cyclopentyl |
| 2-fluorophenyl | cyclohexyl |
| 2-fluorophenyl | cycloheptyl |
| 2-fluorophenyl | (S) bicyclo[2.2.1]heptan-2-yl |
| 2-fluorophenyl | 2,6,6-trimethylbicyclo[3.1.1]hept-3-yl |
| 2-fluorophenyl | 2-(cyclohex-1-en-1-yl)ethyl 1 |
| 2-fluorophenyl | 3-(pyrrolid-2-one-1-yl)propyl |
| 2-fluorophenyl | tetrahydrofuran-2-yl-methyl |
| 2-fluorophenyl | 2-ethylhex-1-yl |
| 2-fluorophenyl | benzyl |
| 2-fluorophenyl | (2-methylphenyl)methyl |
| 2-fluorophenyl | (3-methylphenyl)methyl |
| 2-fluorophenyl | (4-methylphenyl)methyl |
| 2-fluorophenyl | 1-phenylethyl |
| 2-fluorophenyl | (2-methoxyphenyl)methyl |
| 2-fluorophenyl | (3-methoxyphenyl)methyl |
| 2-fluorophenyl | (4-methoxyphenyl)methyl |
| 2-fluorophenyl | (R)-1-(cyclohexyl) ethyl |
| 2-fluorophenyl | (S)-1-(cyclohexyl) ethyl |
| 2-fluorophenyl | (2-fluorophenyl)methyl |
| 2-fluorophenyl | (3-fluorophenyl)methyl |
| 2-fluorophenyl | (4-fluorophenyl)methyl |
| 2-fluorophenyl | (4-chlorophenyl)methyl |
| 2-fluorophenyl | (2-trifluoromethylphenyl)methyl |
| 2-fluorophenyl | (2-fluoro-6-chlorophenyl)methyl |
| 2-fluorophenyl | 2-phenylethyl |
| 2-fluorophenyl | 2-(3-methoxyphenyl)ethyl |
| 2-fluorophenyl | 2-(4-methoxyphenyl)ethyl |
| 2-fluorophenyl | 2-(3-fluorophenyl)ethyl |
| 2-fluorophenyl | 2-(4-fluorophenyl)ethyl |
| 2-fluorophenyl | 2-(3-chlorophenyl)ethyl |
| 2-fluorophenyl | 2,2 bisphenylmethyl |
| 2-fluorophenyl | 3-phenylpropyl |
| 2-fluorophenyl | 2-(thiophen-2-yl)ethyl |
| 2-fluorophenyl | (S)-(3,3 bisphenyl)propyl |
| 2-fluorophenyl | 4-phenylbut-2-yl |
| 2-fluorophenyl | 2-[N-ethyl-N-(3-methylphenyl)amino]ethyl |
| 2-fluorophenyl | pyridin-2-ylmethyl |
| 2-fluorophenyl | (3,4-methylenedioxyphenyl)methyl |
| 2-fluorophenyl | (S) bicyclo[2.2.1]heptan-2-yl |
| 2-fluorophenyl | phenyl |
| 2-fluorophenyl | 4-methoxyphenyl |
| 2-fluorophenyl | 4-ethoxyphenyl |
| 2-fluorophenyl | 4-phenoxyphenyl |
| 2-fluorophenyl | 2-indanyl |
| 2-fluorophenyl | 4-chlorophenyl |
| 2-fluorophenyl | but-1-yl |
| 3-fluorophenyl | isobut-1-yl |
| 3-fluorophenyl | t-butyl |
| 3-fluorophenyl | pent-3-yl |
| 3-fluorophenyl | cyclopropylmethyl |
| 3-fluorophenyl | cyclobutyl |
| 3-fluorophenyl | cyclopentyl |
| 3-fluorophenyl | cyclohexyl |
| 3-fluorophenyl | cyclohept-3-yl |
| 3-fluorophenyl | cyclooctyl |
| 3-fluorophenyl | 3,3,5-trimethylcyclohexyl |
| 3-fluorophenyl | 2-ethylhex-1-yl |
| 3-fluorophenyl | benzyl |
| 3-fluorophenyl | (2-methylphenyl)methyl |
| 3-fluorophenyl | (3-methylphenyl)methyl |
| 3-fluorophenyl | (4-methylphenyl)methyl |
| 3-fluorophenyl | 1-phenylethyl |
| 3-fluorophenyl | (4-methoxyphenyl)methyl |
| 3-fluorophenyl | (2-fluorophenyl)methyl |
| 3-fluorophenyl | (3-fluorophenyl)methyl |
| 3-fluorophenyl | (2,4-dichlorophenyl)methyl |
| 3-fluorophenyl | (3,4-dichlorophenyl)methyl |
| 3-fluorophenyl | 2-(3-methoxyphenyl)ethyl |
| 3-fluorophenyl | 2-(4-methoxyhenyl)ethyl |

| | |
|---|---|
| 3-fluorophenyl | 2-(3-fluorophenyl)ethyl |
| 3-fluorophenyl | 2-(4-fluorophenyl)ethyl |
| 3-fluorophenyl | 2-(3-chlorophenyl)ethyl |
| 3-fluorophenyl | 2,2-bisphenylethyl |
| 3-fluorophenyl | 3-phenylpropyl |
| 3-fluorophenyl | 3,3-bisphenylpropyl |
| 3-fluorophenyl | 4-phenylbut-2-yl |
| 3-fluorophenyl | 2-(morpholin-4-yl)ethyl- |
| 3-fluorophenyl | 2-(N-ethyl-N-phenyl)aminoethyl |
| 3-fluorophenyl | pyridin-2-ylmethyl |
| 3-fluorophenyl | pyridin-2-ylmethyl |
| 3-fluorophenyl | 1,2-dimethylpropyl |
| 3-fluorophenyl | (3,4-methylenedioxyphenyl)methyl |
| 3-fluorophenyl | (R) bicyclo[2.2.1]heptan-2-yl |
| 3-fluorophenyl | phenyl |
| 3-fluorophenyl | 4-methoxyphenyl |
| 3-fluorophenyl | 4-ethoxyphenyl |
| 3-fluorophenyl | 4-phenoxyphenyl |
| thiophene-2-yl | t-butyl |
| thiophene-2-yl | pent-3-yl |
| thiophene-2-yl | cyclopropylmethyl |
| thiophene-2-yl | 3,3,5-trimethylcyclohexane |
| thiophene-2-yl | (S) bicyclo[2.2.1]heptan-2-yl |
| thiophene-2-yl | tetrahydrofuran-2-ylmethyl |
| thiophene-2-yl | 2-ethylhex-1-yl |
| thiophene-2-yl | benzyl |
| thiophene-2-yl | (2-methylphenyl)methyl |
| thiophene-2-yl | (3-methylphenyl)methyl |
| thiophene-2-yl | (4-methylphenyl)methyl |
| thiophene-2-yl | (2-methoxyphenyl)methyl |
| thiophene-2-yl | (3-methoxyphenyl)methyl |
| thiophene-2-yl | (4-methoxyphenyl)methyl |
| thiophene-2-yl | 1-cyclohexylethyl |
| thiophene-2-yl | (2-fluorophenyl)methyl |
| thiophene-2-yl | (3-fluorophenyl)methyl |
| thiophene-2-yl | (4-fluorophenyl)methyl |
| thiophene-2-yl | 2-phenylethyl |
| thiophene-2-yl | 2-(4-methoxyphenyl)ethyl |
| thiophene-2-yl | 2-(3-fluorophenyl)ethyl |
| thiophene-2-yl | 2-[N-ethyl-N-(3-methylphenyl)amino]ethyl |
| thiophene-2-yl | phenyl |
| 3-fluorophenyl | ethyl |
| phenyl | but-1-yl |
| phenyl | isobut-1-yl |
| phenyl | t-butyl |
| phenyl | pentyl-3-yl |
| phenyl | cyclopropylmethyl |
| phenyl | cyclobutyl-1-yl |
| phenyl | cyclopentyl |
| phenyl | cyclohexyl |
| phenyl | cyclohept-3-yl |
| phenyl | 3,3,5-trimethylcyclohexyl |
| phenyl | (R) bicyclo[2.2.1]heptan-2-yl |
| phenyl | 2,6,6-trimethylbicyclo[3.1.1]hept-3-yl |
| phenyl | 2-(cyclohex-1-en-1-yl)ethyl |
| phenyl | 3-(2-oxopyrrolidin-1-yl)propyl |
| phenyl | tetrahydrofuran-2-ylmethyl |
| phenyl | 2-ethylhex-1-yl |
| phenyl | phenyl |
| phenyl | (2-methylphenyl)methyl |
| phenyl | (3-methylphenyl)methyl |
| phenyl | (4-methylphenyl)methyl |
| phenyl | 1-phenylethyl |
| phenyl | (4-methoxyphenyl)methyl |
| phenyl | (R)-1-cyclohexylethyl |
| phenyl | (S)-1-cyclohexylethyl |
| phenyl | (2-fluorophenyl)methyl |
| phenyl | (3-fluorophenyl)methyl |
| phenyl | (4-fluorophenyl)methyl |
| phenyl | (4-chlorophenyl)methyl |
| phenyl | (2-trifluoromethylphenyl)methyl |
| phenyl | (2-fluoro-6-chlorophenyl)methyl |
| phenyl | (2,4-dichlorophenyl)methyl |
| phenyl | (3,4-dichlorophenyl)methyl |
| phenyl | 2-phenylethyl |
| phenyl | 2-(3-methoxyphenyl)ethyl |
| phenyl | 2-(3-fluorophenyl)ethyl |
| phenyl | 2-(4-fluorophenyl)ethyl |
| phenyl | 2-(3-chlorophenyl)ethyl |
| phenyl | 2,2-bisphenylethyl |
| phenyl | phenylcyclopropyl |
| phenyl | 3-phenylpropyl |
| phenyl | 2-(thiophen-2-yl)ethyl |
| phenyl | 3-dimethylaminopropyl |
| phenyl | 2-(morpholin-4-yl)ethyl |
| phenyl | 1-benzylpiperidin-4-yl |
| phenyl | pyridin-2-yl-methyl |
| phenyl | pyridin-4-yl-methyl |
| phenyl | 3-(imidazol-1-yl)propyl |
| phenyl | (3,4-methylenedioxyphenyl)methyl |
| phenyl | phenyl |
| phenyl | 4-methoxyphenyl |
| phenyl | 4-ethoxyphenyl |
| phenyl | 4-phenoxyphenyl |
| phenyl | 2-indanyl |

| $R^3$ | Combination of R, $R^1$ and the nitrogen atom to which they are attached |
|---|---|
| 2,4-dichlorophenyl | piperidin-1-yl |
| 2,4-dichlorophenyl | 2-ethypiperidin-1-yl |
| 2,4-dichlorophenyl | 4-(piperidin-1-yl)piperidin-1-yl |
| 2,4-dichlorophenyl | 1,2,3,4-tetrahydro-isoquinolin-2-yl |
| 2,4-dichlorophenyl | morpholin-4-yl |
| 2,4-difluorophenyl | 4-methylpiperazin-1-yl |
| 2,4-difluorophenyl | pyrrolidin-1-yl |
| 2,4-difluorophenyl | 4-benzylpiperazin-1-yl |
| 2,4-difluorophenyl | piperidin-1-yl |
| 2,4-difluorophenyl | 4-(piperidin-1-yl)piperidin-1-yl |
| 2,4-difluorophenyl | 1,2,3,4-tetrahydro-isoquinolin-2-yl |
| 2,4-difluorophenyl | morpholin-4-yl |
| 2,4-difluorophenyl | 4-methylpiperazin-1-yl |
| 4-fluorophenyl | 4-benzylpiperazin-1-yl |
| 4-fluorophenyl | piperidin-1-yl |
| 4-fluorophenyl | 2-ethylpiperidin-1-yl |
| 4-fluorophenyl | 4-benzylpiperazin-1-yl |
| 4-fluorophenyl | 4-(piperidin-1-yl)piperidin-1-yl |
| 4-fluorophenyl | 1,2,3,4-tetrahydro-isoquinolin-2-yl |
| 4-fluorophenyl | morpholin-4-yl |
| 4-fluorophenyl | 4-phenlypiperazin-1-yl |
| 4-methyl-1,3-thiazol-2-yl | pyrrolidin-1-yl |
| 4-methyl-1,3-thiazol-2-yl | 4-benzylpiperazin-1-yl |
| 4-methyl-1,3-thiazol-2-yl | piperidin-1-yl |
| 4-methyl-1,3-thiazol-2-yl | 4-benzylpiperazin-1-yl |
| 4-methyl-1,3-thiazol-2-yl | 4-(piperidin-1-yl)piperidin-1-yl |
| 4-methyl-1,3-thiazol-2-yl | 1,2,3,4-tetrahydro-isoquinolin-2-yl |
| 4-methyl-1,3-thiazol-2-yl | morpholin-4-yl |
| 4-methyl-1,3-thiazol-2-yl | 4-methylpiperazino-1-yl |
| 4-methyl-1,3-thiazol-2-yl | 4-phenylpiperazin-1-yl |
| 1,3-benzoxazol-2-yl | pyrrolidin-1-yl |
| 1,3-benzoxazol-2-yl | 2-ethylpiperidin-1-yl |
| 1,3-benzoxazol-2-yl | 4-benzylpiperidin-1-yl |
| 1,3-benzoxazol-2-yl | morpholin-4-yl |
| 1,3-benzoxazol-2-yl | 4-methylpiperazin-1-yl |
| 2-methylphenyl | pyrrolidin-1-yl |
| 2-methylphenyl | piperidin-1-yl |
| 2-methylphenyl | 2-ethylpiperidin-1-yl |
| 2-methylphenyl | 4-benzylpiperidin-1-yl |
| 2-methylphenyl | 4-(piperidin-1-yl)piperidin-1-yl |
| 2-methylphenyl | 1,2,3,4-tetrahydro-isoquinolin-2-yl |
| 2-methylphenyl | morpholin-4-yl |
| 2-methylphenyl | 4-(3,4-dichlorophenyl)piperazin-1-yl |
| 2-methylphenyl | 4-methylpiperazin-1-yl |
| 2-methylphenyl | 4-phenylpiperazin-1-yl |
| 2-chlorophenyl | pyrrolidin-1-yl |
| 2-chlorophenyl | 4-benzylpiperazin-1-yl |
| 2-chlorophenyl | piperidin-1-yl |
| 2-chlorophenyl | 2-ethylpiperidin-1-yl |
| 2-chlorophenyl | 4-benzylpiperidine-1-yl |
| 2-chlorophenyl | 4-(piperidin-1-yl)piperidin-1-yl |
| 2-chlorophenyl | 1,2,3,4-tetrahydro-isoquinolin-2-yl |
| 2-chlorophenyl | morpholin-4-yl |
| 2-chlorophenyl | 4-(3,4-dichlorophenyl)piperazin-1-yl |
| 2-chlorophenyl | 4-methylpiperazin-1-yl |
| 2-chlorophenyl | 4-phenylpiperazin-1-yl |
| 4-chlorophenyl | pyrrolidin-1-yl |
| 4-chlorophenyl | 4-benzylpiperazin-1-yl |
| 4-chlorophenyl | piperidin-1-yl |

-continued

| | |
|---|---|
| 4-chlorophenyl | 2-ethylpiperidin-1-yl |
| 4-chlorophenyl | 4-(piperidin-1-yl)piperidin-1-yl |
| 4-chlorophenyl | 1,2,3,4-tetrahydro-isoquinolin-2-yl |
| 4-chlorophenyl | morpholin-4-yl |
| 4-chlorophenyl | 4-phenylpiperazin-1-yl |
| 2-fluorophenyl | pyrrolidin-1-yl |
| 2-fluorophenyl | 4-benzylpiperazin-1-yl |
| 2-fluorophenyl | piperidin-1-yl |
| 2-fluorophenyl | 2-ethylpiperidin-1-yl |
| 2-fluorophenyl | morpholin-4-yl |
| 2-fluorophenyl | 4-phenylpiperazin-1-yl |
| 2-fluorophenyl | pyrrolidin-1-yl |
| 2-fluorophenyl | 4-benzylpiperazin-1-yl |
| 3-fluorophenyl | piperidin-1-yl |
| 3-fluorophenyl | 4-benzylpiperidin-1-yl |
| 3-fluorophenyl | 1,2,3,4-tetrahydro-isoquinolin-2-yl |
| 3-fluorophenyl | morpholin-4-yl |
| 3-fluorophenyl | 4-methylpiperazin-1-yl |
| 3-fluorophenyl | 4-(piperidin-1-yl)piperidin-1-yl |
| thiophen-2-yl | 4-phenylpiperazin-1-yl |
| thiophen-2-yl | 2-ethylpiperidin-1-yl |
| phenyl | pyrrolidin-1-yl |
| phenyl | 4-benzylpiperazin-1-yl |
| phenyl | piperidin-1-yl |
| phenyl | 2-ethylpiperidin-1-yl |
| phenyl | 4-phenylpiperidin-1-yl |
| phenyl | 4-(piperidin-1-yl)piperidin-1-yl |
| phenyl | morpholin-4-yl |
| phenyl | 4-(3,4-dichlorophenyl)piperazin-1-yl |

The following compounds of Formula I in which R is methyl, $R^1$ is 2-(3,4-dimethoxyphenyl)ethyl, $R^2$ is hydrogen, and X and Y are covalent bonds were also prepared:
$R^3$ is 2,6-dichlorophenyl;
$R^3$ is 4-methylthiazol-2-yl;
$R^3$ is 1,3-benzoxazol-2-yl;
2-methylphenyl;
$R^3$ is 2-chlorophenyl; and
$R^3$ is 4-chlorophenyl.

D. Preparation of a Compound of Formula I, Varying $R^1$, $R^2$ $R^3$, $R^4$, $R^5$, X and Y Similarly, following the procedure of 4A above, but optionally replacing (9-{(4S,1R,2R,5R)-4-[(2-fluorophenylthio)methyl]-7,7-dimethyl-3,6,8-trioxabicyclo[3.3.0]oct-2-yl}purin-6-yl)cyclopentylamine with other compounds of formula (4), other compounds of Formula I are made.

Compounds of Formula I were alternatively made in a combinatorial fashion, as shown in Reaction Scheme II above. Examples 5–8 detail the preparation of a single compound using this technology, but the process was utilized to provide parallel syntheses of multiple compounds of Formula I in a combinatorial manner.

EXAMPLE 5

Preparation of a Compound of Formula (5)

A. Preparation of a Compound of Formula (5) in which $R^2$ is Hydrogen (5)

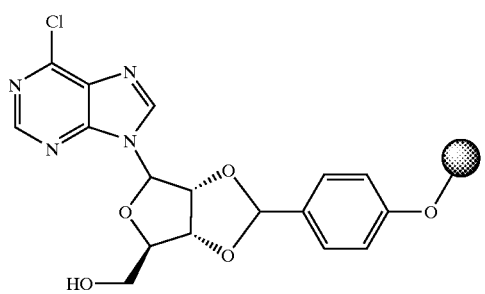

p-Benzyloxybenzaldehyde polystyrene resin (1) (100 g, 3.0 mmol/g, 0.3 mol, 150–300 μm, Polymer Labs) was suspended in dry trimethylorthoformate (1 L). p-Toluenesulfonic acid monohydrate (5.70 g, 0.03 mol, 0.1 eq) was added and the suspension shaken at room temperature for 48 hours. Triethylamine (60 mL) was added, and the resin was promptly filtered, washed 4× with methylene chloride containing 1% triethylamine, and dried under vacuum for 24 hours to afford the dimethylacetal resin Dimethylacetal resin (20.0 g, 3 mmol/g, 60.0 mmol) was suspended in anhydrous N,N-dimethylacetamide (300 mL), and treated sequentially with the riboside of formula (1) (34.4 g, 120 mmol, 2 eq) and 10-camphorsulfonic acid (2.78 g, 12.0 mmol, 0.2 eq.). The mixture was shaken at 200 rpm at room temperature for 96 hours. Triethylamine (4.2 mL, 30.0 mmol, 0.5 eq) was then added and the resin promptly filtered, washed once with N,N-dimethylacetamide, washed with four alternating cycles of methylene chloride containing 1% $Et_3N$ and MeOH containing 1% triethylamine, and finally by three washes with methylene chloride containing 1% triethylamine. The recovered resin was dried under vacuum for 48 hours to provide the resin-bound riboside of formula (5).

EXAMPLE 6

Preparation of a Compound of Formula (6)

A. Preparation of a Compound of Formula (6) in which R and $R^2$ are Hydrogen, Y is a Covalent Bond, and $R^1$ is Cyclopentyl (6)

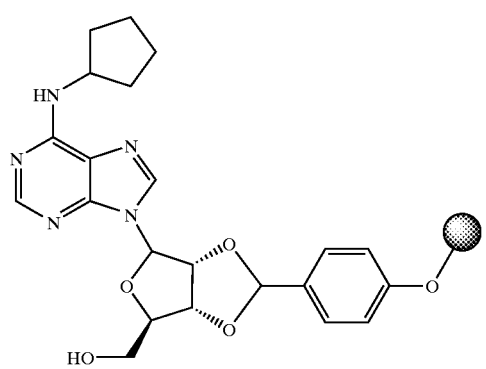

In a reaction vessel was placed the resin-bound riboside of formula (5) (30 mg resin; resin loading 1.5 mmol/g) suspended in anhydrous 1,4-dioxane (30 mL). Diisopropylethylamine (2.4 mL, 13.5 mmol, 20 eq) and excess cyclopentylamine were then added. The reaction vessel was heated at 80° C. for 48 hours with no stirring or agitation. After cooling to room temperature the solvent was removed, and methanol containing 1% triethylamine (50 mL) was added to shrink the resin. The product was washed with four alternating cycles of methanol containing 1% triethylamine and methylene chloride containing 1% triethylamine, and dried overnight in vacuo to provide the resin-bound compound of formula (6).

EXAMPLE 7

Preparation of a Compound of Formula (7)

A. Preparation of a Compound of Formula (7) in which R and R² are Hydrogen, Y is a Covalent Bond, and R¹ is Cyclopentyl and R³ is 2-Flurophenyl (7)

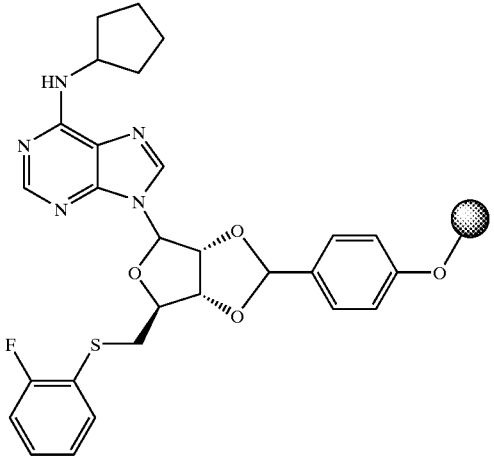

The product from Example 6 was suspended in anhydrous pyridine (2 mL) and treated with diisopropylethylamine (0.13 mL). After cooling to 0° C., methanesulfonyl chloride (0.035 mL, 337 mmol) was added dropwise. The reaction mixture was agitated regularly by hand during the addition. After 90 minutes the reaction mixture was warmed to room temperature and shaken for 24 hours. After removal of the reaction mixture, the product was rinsed with anhydrous methylene chloride containing 1% triethylamine and treated with methanol containing 1% triethylamine to shrink the resin, to provide a mesylated derivative of the resin-bound compound of formula (6).

The mesylate was then suspended in acetonitrile (1.5 mL) and treated with excess diisopropylethylamine (0.16 mL) followed by water (0.7 mL) and 2-fluorothiophenol (45 mmol). The reaction vessel was warmed to approximately 80° C. without agitation for 65 hours. The product was washed with four alternating cycles of methanol containing 1% triethylamine and methylene chloride containing 1% triethylamine, and dried overnight in vacuo, to provide a resin bound compound of formula (7).

EXAMPLE 8

Preparation of a Compound of Formula I

A. Preparation of a Compound of Formula I in which R is Hydrogen, R¹ is Cyclopentyl, R² is Hydrogen, R³ is 2-Fluorophenyl, and X and Y are Covalent Bonds

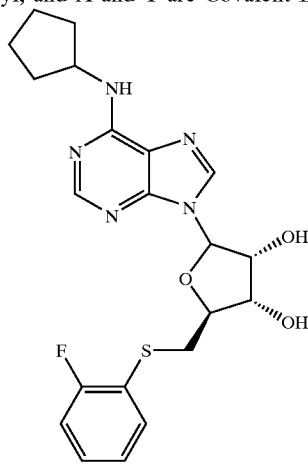

The resin bound compound of formula (7) was suspended in a solution of 2% trifluoroacetic acid/5% methanol/methylene chloride and shaken (200 rpm) at room temperature for 2 hours. After removal of the solution, the residue was rinsed with methylene chloride (3×0.5 mL), and the combined filtrates were concentrated under reduced pressure to afford (4S,5S,3R)-2-[6-(cyclopentylamino)purin-9-yl]-5-[(2-fluorophenylthio)methyl]oxolane-3,4-diol, a compound of Formula I.

EXAMPLE 9

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 10

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 11

A dry powder inhaler formulation is prepared containing the following components:

Formula I

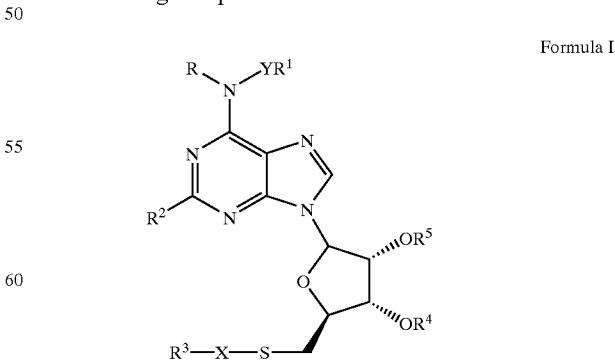

The active ingredient is mixed with the lactose and the mixture is added to a dry powder inhaling appliance.

EXAMPLE 12

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 13

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 14

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 15

A subcutaneous formulation may be prepared as follows:

| Ingredient | Quantity |
|---|---|
| Active Ingredient | 5.0 mg |
| Corn Oil | 1.0 mL |

EXAMPLE 16

An injectable preparation is prepared having the following composition:

| Ingredients | Amount |
|---|---|
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 17

A topical preparation is prepared having the following composition:

| Ingredients | grams |
|---|---|
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 18
Sustained Release Composition

| Ingredient | Weight Range (%) | Preferred Range (%) | Most Preferred |
|---|---|---|---|
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl, methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 19

Binding Assays—$DDT_1$ Cells

Cell Culture

DDT cells (hamster vas deferens smooth muscle cell line) were grown as monolayers in petri dishes using Dulbecco's Modified Eagle's Medium (DMEM) containing 2.5 $\mu g\ ml^{-1}$ amphotericin B, 100 U $ml^{-1}$ penicillin G, 0.1 mg $ml^{-1}$ streptomycin sulfate and 5% fetal bovine serum in a humidified atmosphere of 95% air and 5% $CO_2$. Cells were subcultured twice weekly by dispersion in Hank's Balanced Salt Solution (HBSS) without the divalent cations and containing 1 mM EDTA. The cells were then seeded in growth medium at a density of $1.2 \times 10^5$ cells per plate and experiments were performed 4 days later at approximately one day preconfluence.

Membrane Preparations

Attached cells were washed twice with HBSS (2×10 ml), scraped free of the plate with the aid of a rubber policeman in 5 ml of 50 mM Tris-HCl buffer pH 7.4 at 4° C. and the suspension homogenized for 10 s. The suspension was then centrifuged at 27,000×g for 10 min. The pellet was resuspended in homogenization buffer by vortexing and centrifuged as described above. The final pellet was resuspended in 1 vol of 50 mM Tris-HCl buffer pH 7.4 containing 5 mM $MgCl_2$ for $A_1$ AdoR assays. For the [$^{35}$S]GTPγS binding assay the final pellet was resuspended in 50 mM Tris-HCl pH 7.4 containing 5 mM $MgCl_2$, 100 mM NaCl and 1 mM dithiothreitol. This membrane suspension was then placed in liquid nitrogen for 10 min, thawed and used for assays. The protein content was determined with a Bradford™ Assay Kit using bovine serum albumin as standard.

Competitive Binding Assay

Pig striatum were prepared by homogenation in 50 mM Tris buffer (5× volume of tissue mass pH=7.4). After centrifugation at 19,000 rpm for 25 minutes at 4° C., the supernatant was discarded, and the process was repeated twice. Compounds of Formula I were assayed to determine their affinity for the $A_1$ receptor in a pig striatum membrane prep or a $DDT_1$ membrane prep. Briefly, 0.2 mg of pig striatal membranes or $DDT_1$ cell membranes were treated with adenosine deaminase and 50 mM Tris buffer (pH=7.4) followed by mixing. To the pig membranes was added 2 $\mu L$ of serially diluted DMSO stock solution of the compounds of this invention at concentrations ranging from 100 microM to 10 nM. The control received 2 microL of DMSO alone, then the antagonist [$^3$H] 8-cyclopentylxanthine (CPX) for pig striatum or the agonist [$^3$H] 2-chloro-6-cyclopentyladenosine (CCPA) for $DDT_1$ membranes in Tris buffer (50 mM, pH of 7.4) was added to achieve a final concentration of 2 nM. After incubation at 23 C for 2 h, then the solutions were filtered using a membrane harvester using multiple washing of the membranes (3×). The filter disks were counted in scintillation cocktail affording the amount of displacement of tritiated CPX or by the competitive binding of compounds of Formula I.

The compounds of Formula I were shown to be of high, medium, or low affinity for the $A_1$ adenosine receptor in this assay.

EXAMPLE 20

[$^{35}$S]GTPγS Binding Assays $A_1$-agonist stimulated [$^{35}$S]GTPγS binding was determined by a modification of the method described by Giersckik et al. (1991) and Lorenzen et al. (1993). Membrane protein (30–50 $\mu g$) was incubated in a volume of 0.1 ml containing 50 mM Tris-HCl buffer pH 7.4, 5 mM $MgCl_2$, 100 mM NaCl, 1 mM dithiothreitol, 0.2 units $ml^{-1}$ adenosine deaminase, 0.5% BSA, 1 mM EDTA, 10 mM GDP, 0.3 nM [$^{35}$S]GTPγS and with or without varying concentrations of CPA for 90 min at 30° C. Nonspecific binding was determined by the addition of 10 $\mu M$ GTPγS. Agonist stimulated binding was determined as the difference between total binding in the presence of CPA and basal binding determined in the absence of CPA. Previous reports have shown that agonist stimulated [$^{35}$S]GTPγS binding was dependent on the presence of GDP (Gierschik et al., 1991; Lorenzen et al., 1993; Traynor & Nahorski, 1995). In preliminary experiments, it was found that 10 $\mu M$ GDP gave the optimal stimulation of CPA dependent [$^{35}$S]GTPγS binding and this concentration was therefore used in all studies. In saturation experiments, 0.5 nM [$^{35}$S]GTPγS was incubated with 0.5–1000 nM GTPγS. At the end of the incubation, each suspension was filtered and the retained radioactivity determined as described above.

The compounds of Formula I were shown to be partial or full agonists of the $A_1$ adenosine receptor in this assay.

EXAMPLE 21 cAMP Assay

A scintillation proximity assay (SPA) using rabbit antibodies directed at cAMP using an added tracer of adenosine 3',5'-cyclic phosphoric acid 2'-O-succinyl-3-[$^{125}$I] iodotyrosine methyl ester and fluoromicrospheres containing anti-rabbit specific antibodies as described by Amersham Pharmacia Biotech (Biotrak cellular communication assays). Briefly, DDT$_1$ cells were cultured in clear bottomed 96 well microtiter plates with opaque wells at concentrations between $10^4$ to $10^6$ cells per well in 40 µl of HBSS at 37° C. (5% CO$_2$ and 95% humidity). The partial or full A$_1$ agonists (5 µl) of this invention were incubated at various concentrations with the DDT$_1$ cells in the presence of rolipram (50 µM), and 5 µM forskolin for 10 min at 37° C. The cells were immediately lysed by treatment 5 µl of 10% dodecyltrimethylammonium bromide followed by shaking using microplate shaker. After incubation of the plate for 5 minutes, an immunoreagent solution (150 µl containing equal volumes of tracer, antiserum, and SPA fluorospheres) was added to each well followed by sealing the plate. After 15–20 h at 23° C., the amount of bound [$^{125}$I] cAMP to the fluoromicrospheres was determined by counting in a microtitre plate scintillation counter for 2 minutes. Comparison of counts with standard curves generated for cAMP using a similar protocol afforded the cAMP present after cell lysis.

The compounds of Formula I were shown to be functionally active as A$_1$ agonists with a partial or full decrease in cAMP in this assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound of the formula:

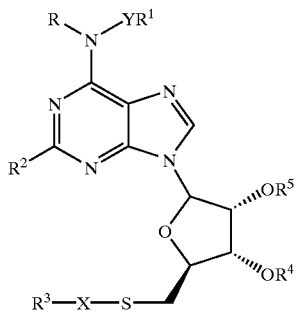

Formula I wherein:

R$^1$ is hydrogen or lower alkyl;

R$^1$ is optionally substituted alkyl, optionally substituted cycloalkyl, optionally substituted aryl, or optionally substituted heteroaryl; or R and YR$^1$ when taken together with the nitrogen atom to which they are attached represents optionally substituted heterocyclyl;

R$^2$ is hydrogen, halo, trifluoromethyl, acyl, or cyano;

R$^3$ is optionally substituted cycloalkyl, optionally substituted aryl; optionally substituted heteroaryl, or optionally substituted heterocyclyl, R$^4$ and R$^5$ are independently hydrogen or acyl; and X and Y are independently a covalent bond or optionally substituted alkylene;

with the proviso that when R$^1$ is methyl and Y is a covalent bond, R$^3$ cannot be phenyl when X is methylene or ethylene.

2. The compound of claim 1, wherein R$^3$ is optionally substituted aryl or optionally substituted heteroaryl.

3. The compound of claim 2, wherein R, R$^2$, R$^4$ and R$^5$ are all hydrogen.

4. The compound of claim 3, wherein R$^3$ is optionally substituted aryl.

5. The compound of claim 4, wherein R$^1$ is optionally substituted cycloalkyl, X is a covalent bond, and R$^3$ is optionally substituted phenyl.

6. The compound of claim 5, wherein Y is a covalent bond, R$^1$ is optionally substituted cyclopentyl and R$^3$ is phenyl substituted by halogen.

7. The compound of claim 6, wherein R$^1$ is 2-hydroxycyclopentyl and R$^3$ is 2-fluorophenyl, namely (4S,5S,2R,3R)-5-[(2-fluorophenylthio)methyl]-2-{6-[(2-hydroxycyclopentyl)amino]-purin-9-yl}oxolane-3,4-diol.

8. The compound of claim 4, wherein Y is optionally substituted lower alkylene, R$^1$ and R$^3$ are both optionally substituted phenyl, and X is a covalent bond.

9. The compound of claim 8, wherein Y is —CH$_2$CH$_2$—, R$^1$ is phenyl, and R$^3$ is 2-methylphenyl.

10. The compound of claim 8, wherein Y is —CH$_2$CH$_2$—, and R$^1$ and R$^3$ are both phenyl.

11. The compound of claim 8, wherein Y is 3-phenylpropylene, R$^1$ is phenyl, and R$^3$ is 2,4-fluorophenyl.

12. The compound of claim 4, wherein X and Y are both covalent bonds, R$^1$ is optionally substituted alkyl or optionally substituted phenyl, and R$^3$ is optionally substituted phenyl.

13. The compound of claim 12, wherein R$^1$ is 2-fluorophenyl, and R$^3$ is phenyl.

14. The compound of claim 12, wherein R$^1$ is pent-3-yl, and R$^3$ is 2-fluorophenyl.

15. The compound of claim 12, wherein R$^1$ is 2-ethylhexyl, and R$^3$ is 2-fluorophenyl.

16. The compound of claim 12, wherein R$^1$ is 2-methylbutyl, and R$^3$ is phenyl.

17. The compound of claim 3, wherein R$^3$ is optionally substituted heteroaryl.

18. The compound of claim 17, wherein X and Y are both covalent bonds, R$^1$ is optionally substituted cycloalkyl, and R$^3$ is optionally substituted 1,3-thiazol-2-yl.

19. The compound of claim 18, wherein R$^1$ is bicyclo[2.2.1]hept-2-yl and R$^3$ is 4-methyl-1,3-thiazol-2-yl.

20. The compound of claim 17, wherein Y is lower alkylene, R$^1$ is optionally substituted cycloalkyl or optionally substituted phenyl, and R$^3$ is optionally substituted 1,3-thiazol-2-yl.

21. The compound of claim 20, wherein Y is ethylene, R$^1$ is 3-chlorophenyl, and R$^3$ is 4-methyl-1,3-thiazol-2-yl.

22. The compound of claim 20, wherein Y is butylen-2-yl, R$^1$ is phenyl, and R$^3$ is 4-methyl-1,3-thiazol-2-yl.

23. The compound of claim 20, wherein Y is methylene, R$^1$ is cyclopropyl, and R$^3$ is 2-methyl-1,3-thiazol-2-yl.

24. The compound of claim 17, wherein Y is methylene, R$^1$ is cyclopropyl, and R$^3$ is 1,3-benzoxazol-2-yl.

25. The compound of claim 2, wherein R$^2$, R$^4$ and R$^5$ are all hydrogen and R and YR$^1$ when taken together with the nitrogen atom to which they are attached represents optionally substituted heterocyclyl.

26. The compound of claim 25, wherein R$^3$ is optionally substituted phenyl or optionally substituted heteroaryl and X is a covalent bond.

27. The compound of claim 26, wherein the optionally substituted heterocyclyl is pyrrolidin-1-yl and R$^3$ is 4-methyl-1,3-thiazol-2-yl.

28. A method of treating a disease state in a mammal that is alleviated by treatment with a partial or full $A_1$ adenosine receptor agonist, comprising administering to a mammal in need thereof a therapeutically effective dose of a compound of Formula I wherein:

| Ingredient | Weight % |
|---|---|
| Active Ingredient | 5 |
| Lactose | 95 |

R is hydrogen or lower alkyl;

$R^1$ is optionally substituted alkyl, optionally substituted cycloalkyl, optionally substituted aryl, or optionally substituted heteroaryl; or R and $YR^1$ when taken together with the nitrogen atom to which they are attached represents optionally substituted heterocyclyl;

$R^2$ is hydrogen, halo, trifluoromethyl, acyl, or cyano;

$R^3$ is optionally substituted cycloalkyl, optionally substituted aryl; optionally substituted heteroaryl, or optionally substituted heterocyclyl, $R^4$ and $R^5$ are independently hydrogen or acyl; and X and Y are independently a covalent bond or optionally substituted alkylene;

with the proviso that when $R^1$ is methyl and Y is a covalent bond, $R^3$ cannot be phenyl when X is methylene or ethylene.

29. The method of claim 28, wherein the disease state is chosen from atrial fibrillation, supraventricular tachycardia and atrial flutter, congestive heart failure, epilepsy, stroke, diabetes, obesity, ischemia, stable angina, unstable angina, cardiac transplant, and myocardial infarction.

30. A pharmaceutical composition comprising at least one pharmaceutically acceptable excipient and a therapeutically effective amount of a compound of Formula I wherein:

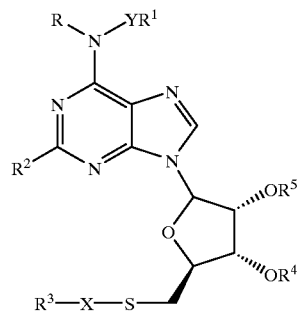

Formula I

R is hydrogen or lower alkyl;

$R^1$ is optionally substituted alkyl, optionally substituted cycloalkyl, optionally substituted aryl, or optionally substituted heteroaryl; or R and $YR^1$ when taken together with the nitrogen atom to which the are attached represents optionally substituted heterocyclyl;

$R^2$ is hydrogen, halo, trifluoromethyl, acyl, or cyano;

$R^3$ is optionally substituted cycloalkyl, optionally substituted aryl; optionally substituted heteroaryl; or optionally substituted heterocyclyl, $R^4$ and $R^5$ are independently hydrogen or acyl; and X and Y are independently a covalent bond or optionally substituted alkylene;

with the proviso that when $R^1$ is methyl and Y is a covalent bond, $R^3$ cannot be phenyl when X is methylene or ethylene.

* * * * *